United States Patent
Chen

(10) Patent No.: US 11,857,940 B2
(45) Date of Patent: *Jan. 2, 2024

(54) HIGH-LEVEL MULTIPLEX AMPLIFICATION

(71) Applicant: Fluidigm Corporation, South San Francisco, CA (US)

(72) Inventor: Peilin Chen, Richmond, CA (US)

(73) Assignee: Fluidigm Corporation, South San Francisco, CA (US)

(*) Notice: Subject to any disclaimer, the term of this patent is extended or adjusted under 35 U.S.C. 154(b) by 182 days.

This patent is subject to a terminal disclaimer.

(21) Appl. No.: 17/398,865

(22) Filed: Aug. 10, 2021

(65) Prior Publication Data

US 2022/0088560 A1    Mar. 24, 2022

Related U.S. Application Data

(63) Continuation of application No. 15/382,360, filed on Dec. 16, 2016, now Pat. No. 11,117,113.

(60) Provisional application No. 62/268,263, filed on Dec. 16, 2015.

(51) Int. Cl.
| | | |
|---|---|---|
| *C12Q 1/6853* | (2018.01) | |
| *C12Q 1/6848* | (2018.01) | |
| *C12Q 1/6844* | (2018.01) | |
| *B01J 19/00* | (2006.01) | |

(52) U.S. Cl.
CPC ........ *B01J 19/0046* (2013.01); *C12Q 1/6844* (2013.01); *C12Q 1/6848* (2013.01); *C12Q 1/6853* (2013.01); *B01J 2219/00585* (2013.01); *B01J 2219/00722* (2013.01)

(58) Field of Classification Search
CPC .................... C12Q 2525/161; C12Q 2525/301
See application file for complete search history.

(56) References Cited

U.S. PATENT DOCUMENTS

| | | | |
|---|---|---|---|
| 4,683,202 | A | 7/1987 | Mullis |
| 5,066,584 | A | 11/1991 | Gyllensten et al. |
| 5,858,671 | A | 1/1999 | Jones |
| 6,605,451 | B1 | 8/2003 | Marmaro et al. |
| 6,824,981 | B2 | 11/2004 | Chait et al. |
| 7,097,980 | B2 | 8/2006 | Barany et al. |
| 7,153,658 | B2 | 12/2006 | Andersen et al. |
| 7,294,503 | B2 | 11/2007 | Quake et al. |

(Continued)

FOREIGN PATENT DOCUMENTS

| | | |
|---|---|---|
| CN | 101067156 A | 11/2007 |
| CN | 103890191 A | 6/2014 |

(Continued)

OTHER PUBLICATIONS

Arendt, D. (2008) "The evolution of cell types in animals: emerging principles from molecular studies." Nature Reviews Genetics 9(11):868-882.

(Continued)

*Primary Examiner* — Teresa E Strzelecka
(74) *Attorney, Agent, or Firm* — Emily M. Haliday; Weaver Austin Villeneuve & Sampson LLP

(57) ABSTRACT

The present disclosure provides a "looping amplification" method to increase the specificity of nucleic acid amplification. This increased specificity facilitates multiplexing to a much higher degree than was previously possible.

14 Claims, 12 Drawing Sheets

Specification includes a Sequence Listing.

(56) References Cited

U.S. PATENT DOCUMENTS

| | | |
|---|---|---|
| 7,312,034 B2 | 12/2007 | Virgos et al. |
| 7,851,148 B2 | 12/2010 | Han |
| 8,318,434 B2 | 11/2012 | Cuppens |
| 8,450,063 B2 | 5/2013 | Dube et al. |
| 8,603,749 B2 | 12/2013 | Gillevet |
| 8,617,817 B2 | 12/2013 | Getts et al. |
| 8,628,923 B2 | 1/2014 | Hamilton et al. |
| 8,691,509 B2 | 4/2014 | May et al. |
| 8,697,363 B2 | 4/2014 | Mir et al. |
| 9,074,204 B2 | 7/2015 | Anderson et al. |
| 9,175,339 B2 | 11/2015 | Kawase et al. |
| 9,440,231 B2 | 9/2016 | West et al. |
| 9,523,117 B2 | 12/2016 | Park et al. |
| 9,540,681 B2 | 1/2017 | Chun et al. |
| 9,677,119 B2 | 6/2017 | May et al. |
| 9,938,641 B2 | 4/2018 | West et al. |
| 9,944,982 B2 | 4/2018 | Schwartz et al. |
| 10,190,163 B2 | 1/2019 | Conant et al. |
| 10,344,318 B2 | 7/2019 | May et al. |
| 10,501,786 B2 | 12/2019 | Anderson et al. |
| 11,117,113 B2 | 9/2021 | Chen |
| 2001/0046681 A1 | 11/2001 | Senapathy |
| 2002/0160361 A1 | 10/2002 | Loehrlein et al. |
| 2003/0119004 A1 | 6/2003 | Wenz et al. |
| 2004/0005594 A1 | 1/2004 | Holliger et al. |
| 2004/0081993 A1 | 4/2004 | Cantor et al. |
| 2004/0086892 A1 | 5/2004 | Crothers et al. |
| 2004/0091879 A1 | 5/2004 | Nolan et al. |
| 2004/0110153 A1 | 6/2004 | Dong et al. |
| 2004/0110191 A1 | 6/2004 | Winkler et al. |
| 2004/0112442 A1 | 6/2004 | Maerkl et al. |
| 2004/0185490 A1 | 9/2004 | Huang et al. |
| 2004/0191823 A1 | 9/2004 | Virgos et al. |
| 2004/0209299 A1 | 10/2004 | Pinter et al. |
| 2004/0229349 A1 | 11/2004 | Daridon |
| 2005/0064488 A1 | 3/2005 | Huh et al. |
| 2005/0095634 A1 | 5/2005 | Baker et al. |
| 2005/0170373 A1 | 8/2005 | Monforte |
| 2005/0252773 A1 | 11/2005 | McBride et al. |
| 2005/0260640 A1 | 11/2005 | Andersen et al. |
| 2006/0040283 A1 | 2/2006 | Xiang et al. |
| 2006/0040297 A1 | 2/2006 | Leamon et al. |
| 2006/0053503 A1 | 3/2006 | Culiat et al. |
| 2006/0088872 A1 | 4/2006 | Ahmadian et al. |
| 2006/0105380 A1 | 5/2006 | Slepnev |
| 2006/0194225 A1 | 8/2006 | Spier |
| 2006/0263789 A1 | 11/2006 | Kincaid |
| 2007/0020640 A1 | 1/2007 | McCloskey et al. |
| 2007/0074972 A1 | 4/2007 | Nassef et al. |
| 2007/0077570 A1 | 4/2007 | Lao et al. |
| 2007/0172873 A1 | 7/2007 | Brenner et al. |
| 2007/0219364 A1 | 9/2007 | Andersen et al. |
| 2007/0224613 A1 | 9/2007 | Strathmann |
| 2008/0090239 A1 | 4/2008 | Shoemaker et al. |
| 2008/0108063 A1 | 5/2008 | Lucero et al. |
| 2008/0131937 A1 | 6/2008 | Schroeder |
| 2008/0223721 A1 | 9/2008 | Cohen et al. |
| 2009/0053719 A1 | 2/2009 | Lo et al. |
| 2009/0098555 A1 | 4/2009 | Roth et al. |
| 2009/0163366 A1 | 6/2009 | Nickerson et al. |
| 2009/0170713 A1 | 7/2009 | van Eijk et al. |
| 2009/0233291 A1 | 9/2009 | Chen et al. |
| 2009/0233802 A1 | 9/2009 | Bignell et al. |
| 2009/0239308 A1 | 9/2009 | Dube et al. |
| 2009/0317798 A1 | 12/2009 | Heid et al. |
| 2010/0021984 A1 | 1/2010 | Edd et al. |
| 2010/0022414 A1 | 1/2010 | Link et al. |
| 2010/0035763 A1 | 2/2010 | Chen et al. |
| 2010/0041563 A1 | 2/2010 | Li et al. |
| 2010/0069250 A1 | 3/2010 | White, III et al. |
| 2010/0120038 A1 | 5/2010 | Mir et al. |
| 2010/0143908 A1 | 6/2010 | Gillevet |
| 2010/0178655 A1 | 7/2010 | Hamilton et al. |
| 2010/0203538 A1 | 8/2010 | Dube et al. |
| 2010/0273219 A1 | 10/2010 | May et al. |
| 2010/0285537 A1 | 11/2010 | Zimmermann |
| 2010/0285975 A1 | 11/2010 | Mathies et al. |
| 2011/0000560 A1 | 1/2011 | Miller et al. |
| 2011/0053806 A1 | 3/2011 | Amin |
| 2011/0129841 A1 | 6/2011 | Heid et al. |
| 2011/0143949 A1 | 6/2011 | Heid et al. |
| 2011/0207134 A1 | 8/2011 | Faham et al. |
| 2012/0034685 A1 | 2/2012 | Sparks et al. |
| 2012/0220494 A1 | 8/2012 | Samuels et al. |
| 2012/0316074 A1 | 12/2012 | Saxonov |
| 2012/0316075 A1 | 12/2012 | Buzby et al. |
| 2013/0005585 A1* | 1/2013 | Anderson ............ C12Q 1/6874 435/6.12 |
| 2013/0017960 A1 | 1/2013 | Honisch et al. |
| 2013/0137094 A1 | 5/2013 | Espina et al. |
| 2013/0217584 A1 | 8/2013 | Zhang et al. |
| 2013/0323732 A1 | 12/2013 | Anderson et al. |
| 2014/0087973 A1 | 3/2014 | Amin |
| 2014/0154679 A1 | 6/2014 | Dube et al. |
| 2014/0186827 A1 | 7/2014 | Pieprzyk et al. |
| 2014/0193812 A1 | 7/2014 | Hamilton et al. |
| 2014/0227691 A1 | 8/2014 | May et al. |
| 2014/0272952 A1 | 9/2014 | May et al. |
| 2014/0296090 A1 | 10/2014 | Mir et al. |
| 2014/0308669 A1 | 10/2014 | Yang et al. |
| 2014/0322716 A1 | 10/2014 | Robins |
| 2015/0299784 A1 | 10/2015 | Fan et al. |
| 2015/0307874 A1 | 10/2015 | Jaitin et al. |
| 2016/0208322 A1 | 7/2016 | Anderson et al. |
| 2016/0244742 A1 | 8/2016 | Linnarsson et al. |
| 2016/0251714 A1 | 9/2016 | Conant et al. |
| 2016/0340728 A1 | 11/2016 | Hamilton et al. |
| 2017/0043340 A1 | 2/2017 | West et al. |
| 2017/0175170 A1 | 6/2017 | Chen |
| 2017/0349934 A1 | 12/2017 | May et al. |
| 2019/0185929 A1 | 6/2019 | Conant et al. |
| 2020/0102594 A1 | 4/2020 | May et al. |
| 2021/0254044 A1 | 8/2021 | Linnarsson et al. |
| 2021/0324446 A1 | 10/2021 | May et al. |
| 2022/0119874 A1 | 4/2022 | Anderson et al. |

FOREIGN PATENT DOCUMENTS

| | | |
|---|---|---|
| CN | 104619862 A | 5/2015 |
| EP | 0197196 A1 | 10/1986 |
| EP | 2201143 B1 | 11/2012 |
| EP | 2746395 A1 | 6/2014 |
| WO | WO-9617954 A1 | 6/1996 |
| WO | WO-9746704 A1 | 12/1997 |
| WO | WO-0159161 A2 | 8/2001 |
| WO | WO-02081729 A2 | 10/2002 |
| WO | WO-03060159 A2 | 7/2003 |
| WO | WO-2004040001 A2 | 5/2004 |
| WO | WO-2004051218 A2 | 6/2004 |
| WO | WO-2004081183 A2 | 9/2004 |
| WO | WO-2005003394 A2 | 1/2005 |
| WO | WO-2005064020 A1 | 7/2005 |
| WO | WO-2005107938 A2 | 11/2005 |
| WO | WO-2006023919 A2 | 3/2006 |
| WO | WO-2006112780 A1 | 10/2006 |
| WO | WO-2006128010 A2 | 11/2006 |
| WO | WO-2007024798 A2 | 3/2007 |
| WO | WO-2007033385 A2 | 3/2007 |
| WO | WO-2007044091 A2 | 4/2007 |
| WO | WO-2007104816 A2 | 9/2007 |
| WO | WO-2008015396 A2 | 2/2008 |
| WO | WO-2009004335 A1 | 1/2009 |
| WO | WO-2009102896 A2 | 8/2009 |
| WO | WO-2010027870 A2 | 3/2010 |
| WO | WO-2010115154 A1 | 10/2010 |
| WO | WO-2010117620 A2 | 10/2010 |
| WO | WO-2011142836 A2 | 11/2011 |
| WO | WO-2011143659 A2 | 11/2011 |
| WO | WO-2012048341 A1 | 4/2012 |
| WO | WO-2012129363 A2 | 9/2012 |
| WO | WO-2012162267 A2 | 11/2012 |
| WO | WO-2012166425 A2 | 12/2012 |
| WO | WO-2013130674 A1 | 9/2013 |
| WO | WO-2013188872 A1 | 12/2013 |

(56) References Cited

FOREIGN PATENT DOCUMENTS

| WO | WO-2014008447 A1 | 1/2014 |
|---|---|---|
| WO | WO-2014144495 A1 | 9/2014 |
| WO | WO-2014145128 A2 | 9/2014 |
| WO | WO-2015044428 A1 | 4/2015 |
| WO | WO-2016044227 A1 | 3/2016 |
| WO | WO-2016100977 A1 | 6/2016 |
| WO | WO-2017106777 A1 | 6/2017 |
| WO | WO-2018013723 A1 | 1/2018 |

OTHER PUBLICATIONS

Attar et al. (2018) "A practical solution for preserving single cells for RNA sequencing." Scientific Reports 8(1):2151 (5 pages).
Australian Office Action dated May 23, 2014 issued in AU2010232439.
Australian Patent Examination Report No. 1 dated Nov. 22, 2016 issued in AU2015242980.
Benson et al. (2013) "GenBank" Nucleic Acids Research, 41: D36-D42 Database Issue [Published Online Nov. 27, 2012].
Binladen et al. (Feb. 2007) "The use of coded PCR Primers enables High-Throughput Sequencing of multiple homolog amplification products by 454 parallel sequencing," PLOS One, 2(2):e197, 11 pages (Published online Feb. 14, 2007).
Brouzes et al. (Aug. 25, 2009) "Droplet microfluidic technology for single-cell high-throughput screening" PNAS, 106(34):14195-14200.
Brownie, J. et al., "The elimination of primer-dimer accumulation in PCR", Nucleic Acids Research, 1997, vol. 25, No. 16, pp. 3235-3241.
CA Office Action dated Dec. 12, 2022 in Application No. CA3006994.
Canadian Office Action dated Apr. 20, 2018 issued in CA 2,734,868.
Canadian Office Action dated Dec. 5, 2019 issued in CA 3,018,687.
Canadian Office Action dated Feb. 26, 2016 issued in CA 2,757,560.
Canadian Office Action dated Jul. 8, 2015 issued in CA 2,734,868.
Canadian Office Action dated Mar. 16, 2017 issued in CA 2,734,868.
Canadian Office Action dated Mar. 16, 2017 issued in CA 2,757,560.
Casbon et al. (2011) "A method for counting PCR template molecules with application to next-generation sequencing" Nucleic acids research 39(12): e81(8 pages).
Chao et al., (2008) "Microfluidic single-cell analysis of intracellular compounds," J. R. Soc. Interface, Suppl 2, 5:S139-S150.
Chinese Decision of Rejection dated Oct. 21, 2014 issued in CN200980142505.9.
Chinese Decision of Rejection [No Translation] dated Nov. 15, 2017 issued in CN 201280033406.9.
Chinese First Office Action dated Jun. 15, 2015 issued in CN201410139163.8.
Chinese First Office Action dated Mar. 2, 2015 issued in CN201410138786.3.
Chinese First Office Action dated Nov. 1, 2012 issued in CN200980142505.9.
Chinese Fourth Office Action dated Dec. 28, 2016 issued in CN200980142505.9.
Chinese Fourth Office Action dated May 26, 2017 issued in CN201410138786.3.
Chinese Notification of Decision of Rejection dated Feb. 5, 2018 issued in CN201410138786.3.
Chinese Notification of Reexamination dated Jul. 28, 2016 issued in CN200980142505.9.
Chinese Office Action dated Jan. 13, 2014 issued in CN201080021508.X.
Chinese Office Action dated Mar. 4, 2013 issued in CN201080021508.X.
Chinese Office Action [English description & Chinese Office Action] dated May 6, 2015 issued in CN 201280033406.9.
Chinese Office Action [No. Translation] dated Jan. 6, 2017 issued in CN 201280033406.9.
Chinese Office Action [partial English Description] dated Mar. 24, 2016 issued in CN 201280033406.9.
Chinese Reexamination Decision [No translation] dated Nov. 10, 2016 issued in CN200980142505.9.
Chinese Second Office Action dated Apr. 22, 2016 issued in CN201410139163.8.
Chinese Second Office Action dated Dec. 22, 2015 issued in CN201410138786.3.
Chinese Second Office Action dated Sep. 17, 2013 issued in CN200980142505.9.
Chinese Third Office Action dated Apr. 9, 2014 issued in CN200980142505.9.
Chinese Third Office Action dated Sep. 13, 2016 issued in CN201410138786.3.
Chinese Third Office Action [description in English] dated Nov. 2, 2016 issued in CN201410139163.8.
CN Office Action dated Feb. 11, 2023 in Application No. CN20178044623.0 with English translation.
CN Office Action dated Jul. 20, 2022 in Application No. CN20178044623.0 With English translation.
CN Office action dated Jun. 23, 2021, in CN Application No. CN201680074295 with English translation.
CN office action dated Oct. 29, 2021, in application No. CN20178044623.
Dahl et al., "Multigene amplification and massively parallel sequencing for cancer mutation discovery," PNAS USA, May 29, 2007, vol. 104(22), pp. 9387-9392. doi: 10.1073/pnas.0702165104. Epub May 17, 2007.
Darmanis et al. (2016) "Simultaneous Multiplexed Measurement of RNA and Proteins in Single Cells." Cell Rep, 14:380-389.
De Leeneer et al., "Massive parallel amplicon sequencing of the breast cancer genes BRCA1 and BRCA2: opportunities, challenges, and limitations," Human Mutation, Mar. 2011, vol. 32(3), pp. 335-344. doi: 10.1002/humu.21428. Epub Feb. 8, 2011.
Eberwine et al. (1992) "Analysis of gene expression in single live neurons" PNAS 89:3010-4.
Eid et al. (2009) "Real-Time DNA Sequencing from Single Polymerase Molecules" Science 323, 133-138.
Endele et al. (2012) "Molecular live cell bioimaging in stem cell research." Annals of the New York Academy of Sciences 1266:18-27.
Eurasian Office Action dated Jul. 18, 2014 issued in EA201171206.
Eurasian Office Action dated Nov. 27, 2013 issued in EA201171206.
European Decision on Appeal dated Oct. 2, 2017 issued in EP 14 158 911.9.
European Extended Search Report dated Feb. 25, 2020 issued in EP17828411.3.
European Extended Search Report dated Jul. 19, 2012 issued in EP 10 759 511.8.
European Extended Search Report dated May 20, 2015 issued in EP 12 789 957.3.
European Extended Search Report dated Oct. 15, 2012 issued in EP 09 81 2052.0.
European Extended Search Report dated Sep. 16, 2014 issued in EP 14 158 911.9.
European Office Action dated Jul. 15, 2019 issued in EP 16820542.5.
European Office Action dated Mar. 15, 2013 issued in EP 10 759 511.8.
European Office Action dated May 18, 2017 issued in EP 09 81 2052.0.
European Office Action dated May 6, 2016 issued in EP 14 158 911.9.
European Office Action dated May 7, 2020 issued in EP 16820542.5.
European Office Action dated Oct. 21, 2020 issued in EP17828411.3.
European Summons to Attend Oral Proceedings dated Feb. 9, 2017 issued in EP 14 158 911.9.
European Supplementary Partial Search Report dated Nov. 21, 2019 issued in EP17828411.3.
Feschotte et al. (2007) "DNA Transposons and the Evolution of Eukaryotic Genomes," Ann. Rev. Genet., 41: 331-368.

(56) References Cited

OTHER PUBLICATIONS

Fredriksson et al., "Multiplex amplification of all coding sequences within 10 cancer genes by Gene-Collector," Nucleic Acids Research, 2007, vol. 35(7), e47, pp. 1-6. doi: 10.1093/nar/gkm078. Epub Feb. 22, 2007.
Fu et al. (2011) "Counting individual DNA molecules by the stochastic attachment of diverse labels" PNAS 108(22):9026-31.
Gill et al. (2008) "Nucleic Acid Isothermal Amplification Technologiesa Review" Nucleosides, Nucleotides, and Nucleic Acids, 27:224-243.
Gillevet et al. (May 2010) "Quantitative Assessment of the Human Gut Microbiome using Multitag Pyrosequencing," Chem Biodivers. 7(5):1065-1075; NIH Public Access, Author Manuscript, doi:10.1002/cbdv.200900322 (14 pages).
Goetz et al. (2012) "Transcriptome sequencing of single cells with Smart-Seq." Nature biotechnology 30: 763-5.
Grunenwald et al. (2001) "Prepare Custom EZ::TN™ Transposons by PCR Using Primers with Transposase-Specific Mosaic End (ME) Sequences" Epicenter Forum 8(3): 4-5.
Guo et al. (2003) "Methodology for using a universal primer to label amplified DNA segments for molecular analysis," Biotechnology Letters, 25:2079-2083.
Hamady M. et al., "Error-correcting barcoded primers for pyrosequencing hundreds of samples in multiplex," Nature Method, Mar. 2008, vol. 5(3) :235-237. doi: 10.1038/nmeth.1184. Epub Feb. 10, 2008, p. 235.
Han A., et al., "Linking T-Cell Receptor Sequence to Functional Phenotype at the Single-Cell Level," Nature Biotechnology, 2014, vol. 32(7), pp. 684-692.
Hardenbol P et al., "Multiplexed genotyping with sequence-tagged molecular inversion probes," Nature Biotechnology, Jun. 2003, vol. 21(6), pp. 673-678 doi: 10.1038/nbt821. Epub May 5, 2003.
Harris et al., (Apr. 4, 2008) "Single-molecule DNA sequencing of a viral genome," Science, 320(5872):106-9.
Hashimshony et al. (2012) "CEL-Seq: single-cell RNA-Seq by multiplexed linear amplification." Cell reports 2:666-73.
Hayden et al. (Feb. 18, 2008) "Multiplex-Ready PCR: A new method for multiplexed SSR and SNP genotyping," BMC Genomics, 9(80):12 pages.
Hoffman et al. (2007) "DNA bar coding and pyrosequencing to identify rare HIV drug resistance mutations," Nucleic Acids Research, 35(13):e91, 8pp (Published online Jun. 18, 2007).
Hug et al. (2002) "Measurement of the Number of Molecules of a Single mRNA Species in a Complex mRNA Preparation," J. Theor. Biol., 221:615-624.
Illumina (2011) "Nextera DNA Sample Preparation Kits" 2 pages Retrieved from Internet:https://dnatech.genomecenter.ucdavis.edu/wp-content/uploads/2013/10/datasheet_nextera_dna_sample_prep.pdf.
Indian Office Action dated Apr. 18, 2018 issued in IN 7286/CHENP/2011.
Islam et al. (2011) "Characterization of the single-cell transcriptional landscape by highly multiplex RNA-seq" Genome Research, 21(7):1160-1167.
Islam et al. (2012) "Highly multiplexed and strand-specific single-cell RNA 5' end sequencing." Nat Protoc., 7(5):813-828.
Islam et al. (2014) "Quantitative single-cell RNA -seq with unique molecular identifiers" Nature Methods, 11(2):163-166.
Israel Office Action dated Mar. 3, 2014 issued in IL215462 [translation only].
Israel Office Action [Notification of Technical Defects Prior to Allowance of Application] dated Feb. 11, 2015 issued in IL215462.
Japanese Final Rejection dated Jul. 17, 2015 issued in JP2012-503757.
Japanese Final Rejection dated Mar. 18, 2016 issued in JP2012-503757.
Japanese Office Action dated Aug. 14, 2017 issued in JP2016-152729.
Japanese Office Action dated Aug. 25, 2014 issued in JP2012-503757.
Jiang et al. (2014) "An ID card for T cells," Nature Biotech., 32(7):639-640.
Johnston et al. (2012) "Mitochondrial Variability as a Source of Extrinsic Cellular Noise" PLoS computational biology 8(3):e1002416(14 pages).
Kaper et al. (Apr. 19, 2010) "Parallel preparation of targeted resequencing libraries from 480 genomic regions using multiplex PCR on the Access Array system," AACR 2010 Abstract & presentation, 3 pages.
Kim et al. (2007) "Polony Multiplex Analysis of Gene Expression (PMAGE) in Mouse Hypertrophic Cardiomyopathy," Science 316: 1481-1484.
Kinde et al. (2011) "Detection and quantification of rare mutations with massively parallel sequencing" PNAS 108(23):9530-9535.
Kita-Matsuo et al. (2005) "Adaptor-tagged competitive polymerase chain reaction: amplification bias and quantified gene expression levels," Analytical Biochemistry, 339(1):15-28.
Kivioja et al. (2011) "Counting absolute numbers of molecules using unique molecular identifiers" Nature Methods 9, 72-4.
Klein et al. (2002) "Combined transcriptome and genome analysis of single micrometastatic cells." Nature biotechnology 20(4):387-92.
Korean Notice of Allowance dated Nov. 20, 2017 issued in KR 10-2017-7022769.
Korean Office Action dated Aug. 17, 2016 issued in KR 10-2011-7025826.
Krishnakumar S et al., "A comprehensive assay for targeted multiplex amplification of human DNA sequences," PNAS USA. Jul. 8, 2008, vol. 105(27): 9296-9301. Published online Jul. 2, 2008. doi: 10.1073/pnas.0803240105.
Kurimoto et al. (2006) "An improved single-cell cDNA amplification method for efficient high-density oligonucleotide microarray analysis" Nucleic Acids Research 34(5):e42 (17 pages).
Life Technologies (Feb. 10, 2011) "Ion Torrent Amplicon Sequencing," 6 Pages.
Makrigiorgos et al. (2002) "A PCR-based amplification method retaining the quantitative difference between two complex genomes," Nature Biotechnology, 20:936-39 (Published online: Aug. 5, 2002, doi:1 0.1 038/nbt724).
Maleszka et al. (1997) "Molecular cloning, by a novel approach, of a cDNA encoding a putative olfactory protein in the labial palps of the moth *Cactoblastis cactorum*." Gene 202(1-2):39-43.
Marcus et al., (2006) "Microfluidic single-cell mRNA isolation and analysis," and Supporting information for: Microfluidic single cell mRNA isolation and analysis, Anal. Chem., 78(9):3084-3089 (14 pages).
Marcus,(2006) "Single Cell Gene Expression Analysis Using Microfluidics," dissertation, [available at http://thesis.library.caltech.edu/2755/, deposited Jul. 12, 2006]; also entitled "Single mammalian cell gene expression analysis using microfluidics," 179pp.
Marcy et al. (2007) "Nanoliter Reactors Improve Multiple Displacement Amplification of Genomes from Single Cells" PLOS Genetics 3(9): e155 [1702-1708] with Supplemental Materials and Methods [9 pages].
Meyer M et al., "Parallel tagged sequencing on the 454 platform," Nature Protocols, 2008, vol. 3(2), pp. 267-278. doi: 10.1038/nprot.2007.520.
Morrissy A S et al., "Next-generation tag sequencing for cancer gene expression profiling," Genome Research, Oct. 2009, vol. 19(10), pp. 1825-1835. doi: 10.11 01/gr.094482.109.
Mueller et al. (2011) "One-Step Preservation of Phosphoproteins and Tissue Morphology at Room Temperature for Diagnostic and Research Specimens," PLos ONE, 6(8) e23780 [7 pages].
Neilan et al. (1997) "A universal procedure for primer labelling of amplicons," Nucleic Acids Research, 25(14):2938-2939.
Nextera DNA Sample Preparation Kits, Illumina, 2 pages, https://dnatech.genomecenter.ucdavis.edu/wp-content/uploads/2013/10/datasheet_nextera_dna_sample_prep.pdf.
Novak et al., (Jan. 10, 2011) "Single Cell Multiplex Gene Detection and Sequencing Using Microfluidically-Generated Agarose Emulsions," Angew Chem Int Ed Engl. 50(2): 390-395.

(56) References Cited

OTHER PUBLICATIONS

Ottesen et al., (2006) "Microfluidic Digital PCR Enables Multigene Analysis of Individual Environment Bacteria," Science, 314:1464-1467.
Parameswaran et al. (2007) "A pyrosequencing-tailored nucleotide barcode design unveils opportunities for large-scale sample multiplexing," Nucleic Acids Research, 35(19):e130, 31 pages (Published online Oct. 11, 2007).
PCT International Preliminary Examination Report dated Mar. 10, 2011 issued in PCT/US2009/055083 [WO/2010/027870].
PCT International Preliminary Examination Report dated Oct. 13, 2011 issued in PCT/US2010/029854 [WO/2010/115154].
PCT International Preliminary Report on Patentability dated Apr. 5, 2016 issued in PCT/EP2014/070824 [WO/2015/044428].
PCT International Preliminary Report on Patentability dated Apr. 8, 2014 issued in PCT/US2012/038894 [WO/2012/162267].
PCT International Preliminary Report on Patentability dated Jan. 15, 2019 issued in PCT/US2017/041770.
PCT International Preliminary Report on Patentability dated Jun. 19, 2018 issued in PCT/US2016/067368 [WO/2017/106777].
PCT International Search Report and Written Opinion dated Apr. 10, 2017 issued in PCT/US2016/067368 [WO/2017/106777].
PCT International Search Report and Written Opinion dated Aug. 30, 2010 issued in PCT/US2010/029854 [WO/2010/115154].
PCT International Search Report and Written Opinion dated Dec. 7, 2012 issued in PCT/US2012/038894 [WO/2012/162267].
PCT International Search Report and Written Opinion dated Jan. 13, 2015 issued in PCT/EP2014/070824 [WO/2015/044428].
PCT International Search Report and Written Opinion dated May 10, 2010 issued in PCT/US2009/055083 [WO/2010/027870].
PCT International Search Report and Written Opinion dated Oct. 25, 2017 issued in PCT/US2017/041770.
Peng Q et al., "Reducing amplification artifacts in high multiplex amplicon sequencing by using molecular barcodes," BMC Genomics, Aug. 7, 2015, vol. 16(1):589. pp. 1-12 doi: 10.1186/s12864-015-1806-8.
Porreca et al., "Multiplex amplification of large sets of human exons," Nature Methods, Nov. 2007, vol. 4(11):931-936. doi: 10.1038/nmeth1110. Epub Oct. 14, 2007.
Raj et al. (2006) "Stochastic mRNA Synthesis in Mammalian Cells" PLOS Biol 4(10):e309(1707-1719).
Raj et al. (2008) "Nature, nurture, or chance: stochastic gene expression and its consequences." Cell 135:216-226.
Rakszewska et al. (2014) "One drop at a time: toward droplet microfluidics as a versatile tool for single-cell analysis," NPG Asia Materials, 6: e133, 11 pages.
Rickert et al., (2004) "Multiplexed Real-Time PCR Using Univeral Reporters," Clin. Chem., 50(9):1680-1683 (9 pages).
Saliba et al., (2014) "Single-cell RNA-seq: advances and future challenges," Nucleic Acids Research, 42(14): 8845-8860 (16 pages).
Sawasaki et al. (2002) "A cell-free protein synthesis system for high-throughput proteomics," PNAS, 99(23):14652-14657.
Schadt et al. (2010) "A window into third-generation sequencing" Human Molecular Genetics 19(22):R227-R240.
Sellner et al. (2004) "MLPA and MAPH: New Techniques for Detection of Gene Deletion," Human Mutation, 23(5):413-419.
Shiroguchi et al. (2012) "Digital RNA sequencing minimizes sequence-dependent bias and amplification noise with optimized single-molecule barcodes" PNAS 109(4):1347-1352.
Shuber, A.P. et al., "A Simplified Procedure for Developing Multiplex PCRs," Genome Research, 1995, vol. 5, pp. 488-493.
Sinclair (1998) "To Bead or Not To Bead: Applications of Magnetic Bead Technology" The Scientist Magazine, available at http://www.thescientist.com/?articles.view/articleNo/18984/title/ToBeadorNot-ToBeadApplication sofMagneticBeadTechnology/Jun. 22, 1998, 7 pages.
Singapore Written Opinion dated Oct. 31, 2013 issued in SG201107142-0.
Smith et al. (2010) "Highly-multiplexed barcode sequencing: an efficient method for parallel analysis of pooled samples" Nucleic Acids Res., 38(13):e142 (7 pages).
Stiller M et al., "Direct multiplex sequencing (DMPS)—a novel method for targeted high-throughput sequencing of ancient and highly degraded DNA," Genome Research, Oct. 2009, vol. 19(10), pp. 1843-1848, doi: 10.1101/gr.095760.109.
Stürzenbaum (1999) "Transfer RNA Reduces the Formation of Primer Artifacts During Quantitative PCR," BioTechniques, 27:50-52.
Stubbington et al. (2016) "T cell fate and clonality inference from single-cell transcriptomes," Nature Methods, 7 pages doi:10.1038/nmeth.3800.
Svec et al. (2013) "Direct cell lysis for single-cell gene expression profiling," Frontiers in Oncology, 3(274): 11 pages doi:10.3389/fonc.2013.00274.
Syed et al., "Next-Generation Sequencing Library preparation :Simultaneous Fragmentation and Tagging Using in Vitro Transposition," Epicentre Biotechnologies, 2009 Vol. 6(11), 2 pages.
Tang et al. (2009) "mRNA-Seq whole-transcriptome analysis of a single cell" Nat Methods 6(5):377-82.
Teo et al. (2002) "Reliable and reproducible LightCycler qPCR for HIV-1 DNA 2-LTR circles," Journal of Immunological Methods, 270:109-118.
Tewhey R et al., "Microdroplet-based PCR enrichment for large-scale targeted sequencing," Nature Biotechnology, Nov. 2009, vol. 27(11), pp. 1025-1031. doi: 10.1038/nbt.1583. Epub Nov. 1, 2009.
Thomsen E.R., et al., "Fixed Single-Cell Transcriptomic Characterization of Human Radial Glial Diversity," Nature Methods, 2016, vol. 13(1), 24 pages.
Uematsu et al. (2001) "Multiplex polymerase chain reaction (PCR) with color-tagged module—shuffling primers for comparing gene expression levels in various cells," Nucleic Acids Research, Oxford University Press, GB 29(16): E84(1-6).
U.S. Appl. No. U.S. Appl. No. 61/605,016, inventors Fowler et al., filed Feb. 29, 2012.
U.S. Final Office Action dated Apr. 8, 2016 issued in U.S. Appl. No. 14/180,262.
U.S. Final Office Action dated Apr. 8, 2020 issued in U.S. Appl. No. 15/025,874.
U.S. Final Office Action dated Aug. 15, 2016 issued in U.S. Appl. No. 14/184,499.
U.S. Final Office Action dated Feb. 12, 2013 issued in U.S. Appl. No. 12/548,132.
U.S. Final Office Action dated Feb. 12, 2019 issued in U.S. Appl. No. 15/382,360.
U.S. Final Office Action dated Mar. 18, 2019 issued in U.S. Appl. No. 14/723,872.
U.S. Final Office Action dated Mar. 25, 2013 issued in U.S. Appl. No. 12/753,703.
U.S. Final office Action dated Nov. 16, 2022 in U.S. Appl. No. 17/065,922.
U.S. Final Office Action dated Nov. 30, 2017 issued in U.S. Appl. No. 14/723,872.
U.S. Final Office Action dated Nov. 6, 2020 issued in U.S. Appl. No. 15/382,360.
U.S. Final Office Action dated Sep. 17, 2014 issued in U.S. Appl. No. 13/476,911.
U.S. Non-Final office Action dated Oct. 27, 2022 in U.S. Appl. No. 17/166,992.
U.S. Non-Final Office Action dated Jun. 13, 2023, in U.S. Appl. No. 17/480,067.
U.S. Non-Final Office Action dated Mar. 17, 2022, in U.S. Appl. No. 17/065,922.
U.S. Notice of Allowance dated Aug. 5, 2019 issued in U.S. Appl. No. 14/723,872.
U.S. Notice of Allowance dated Feb. 19, 2019 issued in U.S. Appl. No. 15/590,998.
U.S. Notice of Allowance dated Feb. 9, 2017 issued in U.S. Appl. No. 14/180,262.
U.S. Notice of Allowance dated Jun. 23, 2023, in U.S. Appl. No. 17/166,992.

(56) References Cited

OTHER PUBLICATIONS

U.S. Notice of Allowance dated Mar. 6, 2015 issued in U.S. Appl. No. 13/476,911.
U.S. Notice of Allowance dated May 10, 2021 issued in U.S. Appl. No. 15/382,360.
U.S. Notice of Allowance dated Nov. 14, 2013 issued in U.S. Appl. No. 12/753,703.
U.S. Notice of Allowance dated Nov. 18, 2013 issued in U.S. Appl. No. 12/548,132.
U.S. Office Action dated Aug. 4, 2020 issued in U.S. Appl. No. 16/414,705.
U.S. Office Action dated Feb. 2, 2016 issued in U.S. Appl. No. 14/184,499.
U.S. Office Action dated Feb. 28, 2014 issued in U.S. Appl. No. 13/476,911.
U.S. Office Action dated Jul. 10, 2013 issued in U.S. Appl. No. 12/753,703.
U.S. Office Action dated Jul. 19, 2017 issued in U.S. Appl. No. 14/723,872.
U.S. Office Action dated Jun. 26, 2019 issued in U.S. Appl. No. 15/025,874.
U.S. Office Action dated Jun. 28, 2012 issued in U.S. Appl. No. 12/753,703.
U.S. Office Action dated Mar. 24, 2020 issued in U.S. Appl. No. 15/382,360.
U.S. Office Action dated May 3, 2012 issued in U.S. Appl. No. 12/548,132.
U.S. Office Action dated Oct. 8, 2019 issued in U.S. Appl. No. 15/382,360.
U.S. Office Action dated Sep. 4, 2018 issued in U.S. Appl. No. 15/382,360.
U.S. Office Action [First Action Interview Office Action Summary] dated Nov. 10, 2015 issued in U.S. Appl. No. 14/180,262.
U.S. Office Action [Pre-interview First Office Action] dated Jul. 15, 2015 issued in U.S. Appl. No. 14/180,262.
U.S. Requirement for Restriction/Election dated Jan. 18, 2017 issued in U.S. Appl. No. 14/723,872.
U.S. Restriction Requirement dated Feb. 23, 2023 in U.S. Appl. No. 17/480,067.
Varley K E et al., "Nested Patch PCR enables highly multiplexed mutation discovery in candidate genes," Genome Research, Nov. 2008, vol. 18(11), pp. 1844-1850. doi: 10.1101/gr.078204.108.
Vickaryous et al. (2006) "Human cell type diversity, evolution, development, and classification with special reference to cells derived from the neural crest" Biological Reviews of the Cambridge Philosophical Society 81(3): 425-55.
Warren, (2008) "Single-Cell Gene-Expression Analysis by Quantitative RT-PCT," dissertation, [available at http://thesis.library.caltech.edu/2996/, deposited Aug. 7, 2007], 225 pages.
Windbichler et al. (2006) "Isolation of specific RNA-binding proteins using the streptomycin—binding RNA aptamer," Nature Protocols, 1(2):638-641.
Xiang et al. (2004) "Using DSP, a reversible cross-linker, to fix tissue sections for immunostaining, microdissection and expression profiling," Nucleic Acids Research, 32(22): e185 [8 pages].
Zhu et al. (2001) "Reverse transcriptase template switching: a SMART approach for full-length CDNA library construction," Biotechniques, 30:892-897.

\* cited by examiner

HIGH-LEVEL MULTIPLEX AMPLIFICATION

CROSS-REFERENCE TO RELATED APPLICATIONS

This application is a continuation of U.S. non-provisional application Ser. No. 15/382,360, filed Dec. 16, 2016, which claims the benefit of U.S. provisional application No. 62/268,263, filed Dec. 16, 2015, each of which is hereby incorporated by reference in its entirety.

INCORPORATION BY REFERENCE OF SEQUENCE LISTING PROVIDED AS A TEXT FILE

The instant application contains a Sequence Listing which has been submitted electronically in ASCII format and is hereby incorporated by reference in its entirety. Said ASCII copy, created on Nov. 30, 2021, is named 2021-11-30_FLUDP022C1US_SeqList_ST25.txt and is 1,170 bytes in size.

STATEMENT AS TO RIGHTS TO INVENTIONS MADE UNDER FEDERALLY SPONSORED RESEARCH AND DEVELOPMENT

Not applicable.

FIELD

The present disclosure relates to generally to the area of nucleic acid amplification. In particular, the disclosure relates to methods and compositions useful in target re-sequencing.

BACKGROUND

Target re-sequencing is merging as an important tool for clinical research, clinical trials, and disease diagnosis. However, DNA library preparation for the target re-sequencing is still very challenging, suffering from low target coverage, low sequencing specificity and high cost. Fluidigm Corporation enables 10-plex per reaction or 480-plex per sample on the Fluidigm Access Array® system, which provides a cost-effective and easy-to-use workflow. In this workflow, the multiplex assays require off-chip barcoding and custom sequencing primers in order to be compatible with Illumina sequencers. Genomic coverage is limited by difficulties in increasing the multiplexing level to higher that 10-plex due to the primer dimer formation and reduced sequencing specificity.

SUMMARY

This disclosure describes a method of dramatically increasing the multiplexing level without sacrificing sequencing specificity. This method can be used, for example, in a targeted sequencing library preparation method Fluidigm ACCESS ARRAY® system to achieve greater than 15,000-plex per reaction at low cost. With "on-chip" barcoding, even more "multiplexing" is possible, because Fluidigm's chips, such as the ACCESS ARRAY™ IFC (Integrated Fluidic Circuit) can carry out thousands of reactions simultaneously.

Various embodiments contemplated herein may include, but need not be limited to, one or more of the following:

Embodiment 1: A method for amplifying one or more target nucleic acids, the method including: contacting sample nucleic acids with a forward primer and a reverse primer for each target nucleic acid, wherein each primer includes a target-specific portion and a common sequence 5' of the target-specific portion; and amplifying the target nucleic acid(s) to produce at least one target amplicon wherein a target nucleotide sequence is flanked by the common sequence on one end and its reverse complement on the other end, whereby a single strand of the target amplicon can form a stem loop structure.

Embodiment 2: The method of embodiment 1, wherein a plurality of target nucleic acids is amplified.

Embodiment 3: The method of any preceding embodiment, wherein a plurality of target nucleic acids is amplified in a single reaction mixture.

Embodiment 4: The method embodiment 3, wherein more than 10 target nucleic acids are amplified in a single reaction mixture.

Embodiment 5: The method of embodiment 4, wherein at least 100 target nucleic acids are amplified in a single reaction mixture.

Embodiment 6: The method of embodiment 5, wherein at least 1000 target nucleic acids are amplified in a single reaction mixture.

Embodiment 7: The method of embodiment 6, wherein at least 5000 target nucleic acids are amplified in a single reaction mixture.

Embodiment 8: The method of any preceding embodiment, wherein fewer than 17,000 target nucleic acids are amplified in a single reaction mixture.

Embodiment 9: The method of any preceding embodiment, wherein the common sequence includes a transposon sequence.

Embodiment 10: The method of embodiment 9, wherein the transposon sequence includes 5'-AGATGTGTNNNA-GAGACAG-3' (SEQ ID NO:1).

Embodiment 11: The method of embodiment 10, wherein the transposon sequence includes 5'-AGATGTGTATAAGA-GACAG-3' (SEQ ID NO:2).

Embodiment 12: The method of any preceding embodiment wherein the forward primer and/or the reverse primer for each target nucleic acid comprise(s) a tag nucleotide sequence 5' of the common sequence.

Embodiment 13: The method of embodiment 12, wherein both primers includes tag nucleotide sequences, and the tag nucleotide sequence in the forward primer is different from the tag nucleotide sequence in the reverse primer.

Embodiment 14: The method of any preceding embodiment, wherein amplification cross-hybridization is suppressed as compared to when amplification is carried out using primers containing only target-specific sequences.

Embodiment 15: The method of any preceding embodiment, wherein the average target amplicon size is greater than when amplification is carried out using primers containing only target-specific sequences.

Embodiment 16: The method of any of embodiments 12-15, wherein the forward or reverse primer includes an additional nucleotide sequence 3' of the tag nucleotide sequence.

Embodiment 17: The method of embodiment 16, wherein the forward primer includes a first additional nucleotide sequence 3' of the tag nucleotide sequence, wherein the first additional nucleotide sequence includes a first binding site for a first DNA sequencing primer.

Embodiment 18: The method of embodiment 17, wherein the reverse primer includes a second additional nucleotide sequence 3' of the tag nucleotide sequence, wherein the second additional nucleotide sequence includes a second binding site for a second DNA sequencing primer.

Embodiment 19: The method of embodiment 18, wherein the forward or reverse primer additionally includes a first flow cell attachment site 5' of the tag nucleotide sequence.

Embodiment 20: The method of any of embodiments 12-19, wherein the amplification is carried out using a third primer, wherein the third primer includes a tag-specific portion and a second additional nucleotide sequence 5' of the tag-specific portion.

Embodiment 21: The method of embodiment 20, wherein the second additional nucleotide sequence includes a barcode nucleotide sequence and/or a second flow cell attachment site.

Embodiment 22: The method of embodiment 21, wherein the second additional nucleotide sequence includes a barcode nucleotide sequence 5' of the tag-specific portion, and a second flow cell attachment site 5' of the barcode nucleotide sequence.

Embodiment 23: The method of embodiment 18, wherein the amplification is carried out using a third primer, wherein the third primer includes a tag-specific portion, a barcode nucleotide sequence 5' of the tag-specific portion, and a second flow cell attachment site 5' of the barcode nucleotide sequence, wherein the amplification produces target amplicons having the structure: 5'-first nucleotide tag-first primer binding site-common sequence-target nucleotide sequence-reverse complement of common sequence-second primer binding site-second nucleotide tag-barcode nucleotide sequence-second flow cell attachment site-3'.

Embodiment 24: The method of any preceding embodiment, wherein amplification is carried out in a plurality of separate reaction mixtures.

Embodiment 25: The method of embodiment 24, wherein amplification is carried out in multiplex within each of the plurality of reaction mixtures.

Embodiment 26: The method of any preceding embodiment, wherein the amplification is carried out in a microfluidic device.

Embodiment 27: The method of embodiment 26, wherein the microfluidic device includes a plurality of reaction chambers.

Embodiment 28: The method of embodiment 27, wherein the microfluidic device includes a matrix-type microfluidic device.

Embodiment 29: The method of any of embodiments 26-28, wherein amplification is carried out in multiplex within each of a plurality of reaction chambers.

Embodiment 30: The method of embodiment 29, wherein more than 10 target nucleic acids are amplified in each of the plurality of reaction chambers.

Embodiment 31: The method of embodiment 30, wherein more than 100 target nucleic acids are amplified in each of the plurality of reaction chambers.

Embodiment 32: The method of any of embodiments 30-31, wherein simultaneous amplifications are carried out for at least 4800 target nucleic acids from a particular sample in the microfluidic device.

Embodiment 33: The method of embodiment 32, wherein simultaneous amplifications are carried out for at least 4800 target nucleic acids from at least 48 samples in the microfluidic device.

Embodiment 34: The method of any of embodiments 26-33, wherein the target amplicons are recovered from the microfluidic device after amplification.

Embodiment 35: The method of any of embodiments 23-34, wherein at least one further nucleotide sequence is added to each of the target amplicons.

Embodiment 36: The method of embodiment 35, wherein the further nucleotide sequence includes a first flow cell attachment site added by amplification of the target amplicons using a forward primer having a portion specific for the first nucleotide tag and a first flow cell attachment site 5' of said tag-specific portion and a reverse primer specific for the second flow cell attachment site.

Embodiment 37: The method of any preceding embodiment, wherein the method is carried out to produce a DNA sequencing library, wherein each member of the library has the structure: 5'-first flow cell attachment site-first nucleotide tag-first primer binding site-common sequence-target nucleotide sequence-reverse complement of common sequence-second primer binding site-second nucleotide tag-barcode nucleotide sequence-second flow cell attachment site-3'.

Embodiment 38: The method of any preceding embodiment wherein amplification is carried out in the presence of 2-pyrrolidinone with or without trehalose.

Embodiment 39: The method of any preceding embodiment, wherein the method additionally includes sequencing the target amplicons.

Embodiment 40: A kit including a primer set, wherein the primer set includes at least two primers selected from any of the primers employed in the method of any of embodiments 1, 9-13, 16-23, 35, and 36.

BRIEF DESCRIPTION OF THE DRAWINGS

FIG. 9A shows a representative image of a gel resulting from Example 4. The "PreAmp" lane shows the result of the first step of 20-cycle PCR amplification to add nucleotide tags and binding sites for DNA sequencing primers. As indicated, each of the 6062 primer pairs was present at a concentration of 2 nanomolar (nM or nm). The three lanes under "Adapter Addition" show the results after the second step of 10-cycle PCR amplification to add DNA sequencing adaptors. The primer concentrations indicated in these three lanes refer to the primer concentrations in the first step of 20-cycle PCR. The expected amplicon size range was 320-380 basepairs (including adaptors). Allowing for overlapped amplicons yields 16,564 possible primer pairs, which would produce an expected amplicon size range of 160-1000 basepairs. A primer concentration of 2 nM for the first step produces a strong post-Adaptor Addition band in the expected amplicon size range of 320-380 bp, indicating that the 6062-plex amplification worked. Lowering the first-step primer concentration to 1 nM or 0.5 nM resulted in increasing amplicon overlapping, with 0.5 nM giving a range of bands in the expected amplicon size range of 160-1000 bp. FIG. 9B shows a Bioanalyzer trace corresponding to the 2 nM lanes from FIG. 9A. The trace with lower peaks is from the PreAmp, 2 nM lane, showing the results after the first step of 20-cycle PCR. The trace with higher peaks is from the Adaptor Addition, 2 nM lane, showing the results after the second step of 10-cycle PCR to add DNA sequencing adaptors. FIG. 9C shows a Bioanalyzer trace corresponding to the Adaptor Addition, 0.5 nM lane, showing the results after the second step of 10-cycle PCR to add DNA sequencing adaptors in the overlapped amplicon situation, showing that amplicons sizes ranged from 160-1000 bp, as expected. FIG. 9D shows the genome mapping rate of 6062-plex in single tube at primer concentration 0.5-2 nM when the libraries were sequenced on Illumina NextSeq 500 sequencer, indicating that very specific amplification is achieved.

DETAILED DESCRIPTION

Definitions

Figure 1:
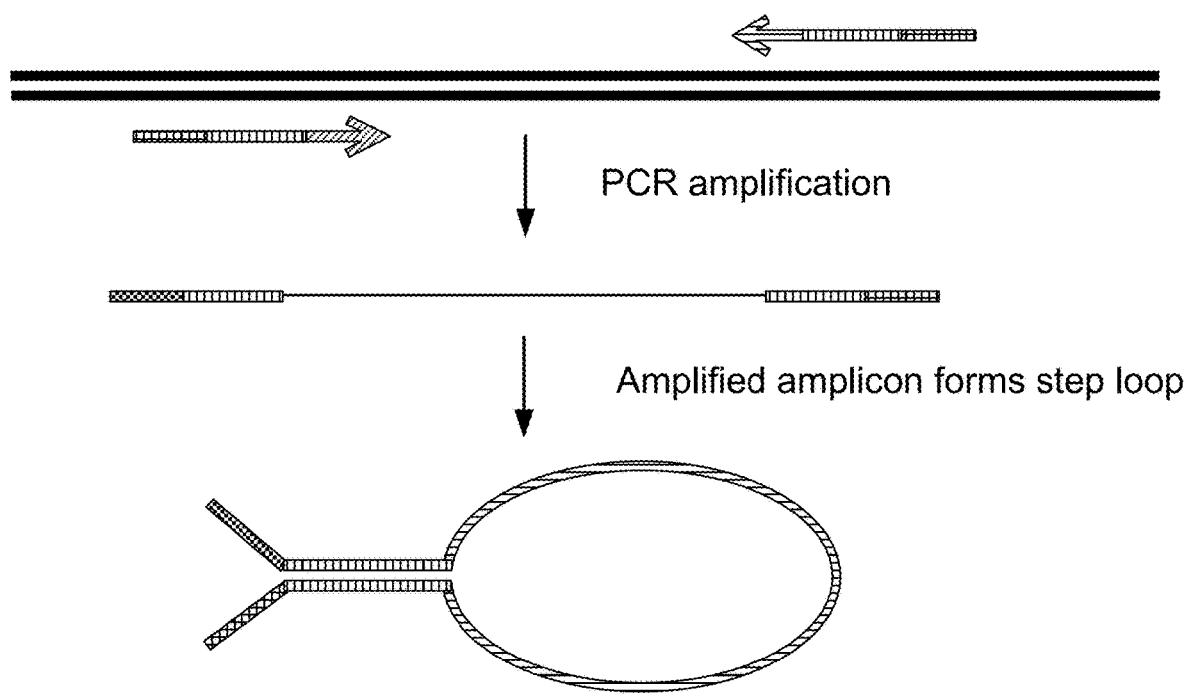
FIG. 1: Stem-loop formation of amplified amplicons. Left-pointing arrow tip: specific reverse primer; right-pointing arrow tip: specific forward primer; vertical line shading: transposon sequence (common sequence), (right) end of left-pointing arrow: tag1; (left) end of right-pointing arrow: tag 2.

Terms used in the claims and specification are defined as set forth below unless otherwise specified. These terms are defined specifically for clarity, but all of the definitions are consistent with how a skilled artisan would understand these terms.

The term "nucleic acid" refers to a nucleotide polymer, and unless otherwise limited, includes known analogs of natural nucleotides that can function in a similar manner (e.g., hybridize) to naturally occurring nucleotides.

The term nucleic acid includes any form of DNA or RNA, including, for example, genomic DNA; complementary DNA (cDNA), which is a DNA representation of mRNA, usually obtained by reverse transcription of messenger RNA (mRNA) or by amplification; DNA molecules produced synthetically or by amplification; mRNA; non-coding RNA; and micro RNA.

The term nucleic acid encompasses double- or triple-stranded nucleic acids, as well as single-stranded molecules. In double- or triple-stranded nucleic acids, the nucleic acid strands need not be coextensive (i.e, a double-stranded nucleic acid need not be double-stranded along the entire length of both strands).

The term nucleic acid also encompasses any chemical modification thereof, such as by methylation and/or by capping. Nucleic acid modifications can include addition of chemical groups that incorporate additional charge, polarizability, hydrogen bonding, electrostatic interaction, and functionality to the individual nucleic acid bases or to the nucleic acid as a whole. Such modifications may include base modifications such as 2'-position sugar modifications, 5-position pyrimidine modifications, 8-position purine modifications, modifications at cytosine exocyclic amines, substitutions of 5-bromo-uracil, backbone modifications, unusual base pairing combinations such as the isobases isocytidine and isoguanidine, and the like.

More particularly, in certain embodiments, nucleic acids, can include polydeoxyribonucleotides (containing 2-deoxy-D-ribose), polyribonucleotides (containing D-ribose), and any other type of nucleic acid that is an N- or C-glycoside of a purine or pyrimidine base, as well as other polymers containing nonnucleotidic backbones, for example, polyamide (e.g., peptide nucleic acids (PNAs)) and polymorpholino (commercially available from the Anti-Virals, Inc., Corvallis, Oregon, as Neugene) polymers, and other synthetic sequence-specific nucleic acid polymers providing that the polymers contain nucleobases in a configuration which allows for base pairing and base stacking, such as is found in DNA and RNA. The term nucleic acid also encompasses linked nucleic acids (LNAs), which are described in U.S. Pat. Nos. 6,794,499, 6,670,461, 6,262,490, and 6,770,748, which are incorporated herein by reference in their entirety for their disclosure of LNAs.

The nucleic acid(s) can be derived from a completely chemical synthesis process, such as a solid phase-mediated chemical synthesis, from a biological source, such as through isolation from any species that produces nucleic acid, or from processes that involve the manipulation of nucleic acids by molecular biology tools, such as DNA replication, PCR amplification, reverse transcription, or from a combination of those processes.

The term "target nucleic acids" is used herein to refer to specific nucleic acids to be detected in the methods of the invention. Although multiple target nucleic acids can be amplified simultaneously, "target nucleic acids" refers to a subset (i.e., something less than) the full complement of nucleic acids present in the reaction mixture.

As used herein the term "target nucleotide sequence" refers to a molecule that includes the nucleotide sequence of a target nucleic acid, such as, for example, the amplification product obtained by amplifying a target nucleic acid or the cDNA produced upon reverse transcription of an RNA target nucleic acid.

As used herein, the term "complementary" refers to the capacity for precise pairing between two nucleotides. I.e., if a nucleotide at a given position of a nucleic acid is capable of forming canonical hydrogen bonding with a nucleotide of another nucleic acid, then the two nucleic acids are considered to be complementary to one another at that position. Complementarity between two single-stranded nucleic acid molecules may be "partial," in which only some of the nucleotides bind, or it may be complete when total complementarity exists between the single-stranded molecules. The degree of complementarity between nucleic acid strands has significant effects on the efficiency and strength of hybridization between nucleic acid strands. A first nucleotide sequence is said to be the "complement" of a second sequence if the first nucleotide sequence is complementary to the second nucleotide sequence. A first nucleotide sequence is said to be the "reverse complement" of a second sequence, if the first nucleotide sequence is complementary to a sequence that is the reverse (i.e., the order of the nucleotides is reversed) of the second sequence.

"Specific hybridization" refers to the binding of a nucleic acid to a target nucleotide sequence in the absence of substantial binding to other nucleotide sequences present in the hybridization mixture under defined stringency conditions. Those of skill in the art recognize that relaxing the stringency of the hybridization conditions allows sequence mismatches to be tolerated.

In particular embodiments, hybridizations are carried out under stringent hybridization conditions. The phrase "stringent hybridization conditions" generally refers to a temperature in a range from about 5° C. to about 20° C. or 25° C. below than the melting temperature ($T_m$) for a specific sequence at a defined ionic strength and pH. As used herein, the $T_m$ is the temperature at which a population of double-stranded nucleic acid molecules becomes half-dissociated into single strands. Methods for calculating the $T_m$ of nucleic acids are well known in the art (see, e.g., Berger and Kimmel (1987) METHODS IN ENZYMOLOGY, VOL. 152: GUIDE TO MOLECULAR CLONING TECHNIQUES, San Diego: Academic Press, Inc. and Sambrook et al. (1989) MOLECULAR CLONING: A LABORATORY MANUAL, 2ND ED., VOLS. 1-3, Cold Spring Harbor Laboratory), both incorporated herein by reference). As indicated by standard references, a simple estimate of the $T_m$ value may be calculated by the equation: $T_m=81.5+0.41(\% G+C)$, when a nucleic acid is in aqueous solution at 1 M NaCl (see, e.g., Anderson and Young, Quantitative Filter Hybridization in NUCLEIC ACID HYBRIDIZATION (1985)). The melting temperature of a hybrid (and thus the conditions for stringent hybridization) is affected by various factors such as the length and nature (DNA, RNA, base composition) of the primer or probe and nature of the target nucleic acid (DNA, RNA, base composition, present in solution or immobilized, and the like), as well as the concentration of salts and other components (e.g., the presence or absence of formamide, dextran sulfate, polyethylene glycol). The effects of these factors are well known and are discussed in standard references in the art. Illustrative stringent conditions suitable for achieving specific hybridization of most sequences are: a temperature of at least about 60° C. and a salt concentration of about 0.2 molar at pH7.

The term "oligonucleotide" is used to refer to a nucleic acid that is relatively short, generally shorter than 200 nucleotides, more particularly, shorter than 100 nucleotides, most particularly, shorter than 50 nucleotides. Oligonucleotides may be single-stranded or double-stranded DNA molecules.

The term "primer" refers to an oligonucleotide that is capable of hybridizing (also termed "annealing") with a nucleic acid and serving as an initiation site for nucleotide (RNA or DNA) polymerization under appropriate conditions (i.e., in the presence of four different nucleoside triphosphates and an agent for polymerization, such as DNA or RNA polymerase or reverse transcriptase) in an appropriate buffer and at a suitable temperature. The appropriate length of a primer depends on the intended use of the primer, but primers are typically at least 7 nucleotides long and, more typically range from 10 to 30 nucleotides, or even more typically from 15 to 30 nucleotides, in length. Other primers can be somewhat longer, e.g., 30 to 50 nucleotides long. In this context, "primer length" refers to the portion of an oligonucleotide or nucleic acid that hybridizes to a complementary target sequence and primes nucleotide synthesis. Short primer molecules generally require cooler temperatures to form sufficiently stable hybrid complexes with the template. A primer need not reflect the exact sequence of the template but must be sufficiently complementary to hybridize with a template. The term "primer site" or "primer binding site" refers to the segment of the template to which a primer hybridizes.

A primer is said to anneal to another nucleic acid if the primer, or a portion thereof, hybridizes to a nucleotide sequence within the nucleic acid. The statement that a primer hybridizes to a particular nucleotide sequence is not intended to imply that the primer hybridizes either completely or exclusively to that nucleotide sequence.

The primer can be perfectly complementary to the target nucleic acid sequence or can be less than perfectly complementary. In certain embodiments, the primer has at least 65% identity to the complement of the target nucleic acid sequence over a sequence of at least 7 nucleotides, more typically over a sequence in the range of 10-30 nucleotides, and often over a sequence of at least 14-25 nucleotides, and more often has at least 75% identity, at least 85% identity, at least 90% identity, or at least 95%, 96%, 97%, 98%, or 99% identity. It will be understood that certain bases (e.g., the 3' base of a primer) are generally desirably perfectly complementary to corresponding bases of the target nucleic acid sequence. Primers typically anneal to the target sequence under stringent hybridization conditions.

The term "primer pair" refers to a set of primers including a 5' "upstream primer" or "forward primer" that hybridizes with the complement of the 5' end of the DNA sequence to be amplified and a 3' "downstream primer" or "reverse primer" that hybridizes with the 3' end of the sequence to be amplified. As will be recognized by those of skill in the art, the terms "upstream" and "downstream" or "forward" and "reverse" are not intended to be limiting, but rather provide illustrative orientation in particular embodiments.

In embodiments in which two primer pairs are used, e.g., in an amplification reaction, the primer pairs may be denoted "inner" and "outer" primer pairs to indicate their relative position; i.e., "inner" primers are incorporated into the reaction product (e.g., an amplicon) at positions in between the positions at which the outer primers are incorporated.

As used herein with reference to a portion of a primer, the term "target-specific portion" refers to a sequence that can specifically anneal to a target nucleic acid or a target nucleotide sequence under suitable annealing conditions.

As used herein with reference to a primer pair, a "common sequence" refers to a sequence that is present in both primers.

The term "tag nucleotide sequence" is used herein to refer to a predetermined nucleotide sequence that is added to a target nucleotide sequence. The nucleotide tag can encode an item of information about the target nucleotide sequence, such the identity of the target nucleotide sequence or the identity of the sample from which the target nucleotide sequence was derived. In certain embodiments, such information may be encoded in one or more nucleotide tags, e.g., a combination of two nucleotide tags, one on either end of a target nucleotide sequence, can encode the identity of the target nucleotide sequence.

As used herein with reference to a portion of a primer, the term "tag-specific portion" refers to a sequence that can specifically anneal to a nucleotide tag under suitable annealing conditions.

The term "transposon" refers to a nucleic acid molecule that is capable of being incorporated in to a nucleic acid by a transposase enzyme. A transposon includes two transposon ends (also termed "arms") linked by a sequence that is sufficiently long to form a loop in the presence of a transposase. Transposons can be double-, single-stranded, or mixed, containing single- and double-stranded region(s), depending on the transposase used to insert the transposon. For Mu, Tn3, Tn5, Tn7 or Tn10 transposases, the transposon ends are double-stranded, but the linking sequence need not be double-stranded. In a transposition event, these transposons are inserted into double-stranded DNA.

The term "transposon end" refers to the sequence region that interacts with transposase. The transposon ends are double-stranded for transposases Mu, Tn3, Tn5, Tn7, Tn10 etc. The transposon ends are single-stranded for transposases IS200/IS605 and ISrad2, but form a secondary structure, just like a double-stranded region. In a transposition event, single-stranded transposons are inserted into single-stranded DNA by a transposase enzyme.

The term "artificial transposon end" refers to a transposon end in which one or more positions in a wildtype transposon end have been substituted with one or more different nucleotides.

The term "transposase" refers to an enzyme that binds to transposon ends and catalyzes their linkage to other double- or single-stranded nucleic acids, such as genomic DNA. Transposases usually comprise an even number of subunits and bind two transposon ends. The two transposon ends can be of identical sequence or of different sequences.

As used herein, the term "barcode nucleotide sequence" is used to refer to nucleotide sequences that encode information. For example, a barcode nucleotide sequence can identify, e.g., the source of the sample nucleic acids under analysis, such as nucleic acids from a particular sample or a particular reaction. Barcodes can be used to distinguish different cells, different treatments, different time points, different positions in space, etc.

The term "stem-loop structure" results from intramolecular base pairing in a single strand of nucleic acid. The structure is also known as a "hairpin" or "hairpin loop" structure. It occurs when two regions of the same strand, usually complementary in nucleotide sequence when read in opposite directions, base-pair to form a double helix with an unpaired loop at one end.

"Amplification" according to the present teachings encompasses any means by which at least a part of at least one target nucleic acid is reproduced, typically in a template-dependent manner, including without limitation, a broad range of techniques for amplifying nucleic acid sequences, either linearly or exponentially. Illustrative means for performing an amplifying step include ligase chain reaction (LCR), ligase detection reaction (LDR), ligation followed by Q-replicase amplification, PCR, primer extension, strand displacement amplification (SDA), hyperbranched strand displacement amplification, multiple displacement amplification (MDA), nucleic acid strand-based amplification (NASBA), 2-step multiplexed amplifications, rolling circle amplification (RCA), and the like, including multiplex versions and combinations thereof, for example but not limited to, OLA/PCR, PCR/OLA, LDR/PCR, PCR/PCR/LDR, PCR/LDR, LCR/PCR, PCR/LCR (also known as combined chain reaction—CCR), and the like. Descriptions of such techniques can be found in, among other sources, Ausbel et al.; PCR Primer: A Laboratory Manual, Diffenbach, Ed., Cold Spring Harbor Press (1995); The Electronic Protocol Book, Chang Bioscience (2002); Msuih et al., J. Clin. Micro. 34:501-07 (1996); The Nucleic Acid Protocols Handbook, R. Rapley, ed., Humana Press, Totowa, N.J. (2002); Abramson et al., Curr Opin Biotechnol. 1993 February; 4(1):41-7, U.S. Pat. Nos. 6,027,998; 6,605,451, Barany et al., PCT Publication No. WO 97/31256; Wenz et al., PCT Publication No. WO 01/92579; Day et al., Genomics, 29(1): 152-162 (1995), Ehrlich et al., Science 252:1643-50 (1991); Innis et al., PCR Protocols: A Guide to Methods and Applications, Academic Press (1990); Favis et al., Nature Biotechnology 18:561-64 (2000); and Rabenau et al., Infection 28:97-102 (2000); Belgrader, Barany, and Lubin, Development of a Multiplex Ligation Detection Reaction DNA Typing Assay, Sixth International Symposium on Human Identification, 1995 (available on the world wide web at: promega.com/geneticidproc/ussymp6proc/blegrad.html); LCR Kit Instruction Manual, Cat. #200520, Rev. #050002, Stratagene, 2002; Barany, Proc. Natl. Acad. Sci. USA 88:188-93 (1991); Bi and Sambrook, Nucl. Acids Res. 25:2924-2951 (1997); Zirvi et al., Nucl. Acid Res. 27:e40i-viii (1999); Dean et al., Proc Natl Acad Sci USA 99:5261-66 (2002); Barany and Gelfand, Gene 109:1-11 (1991); Walker et al., Nucl. Acid Res. 20:1691-96 (1992); Polstra et al., BMC Inf. Dis. 2:18- (2002); Lage et al., Genome Res. 2003 February; 13(2):294-307, and Landegren et al., Science 241:1077-80 (1988), Demidov, V., Expert Rev Mol Diagn. 2002 November; 2(6):542-8., Cook et al., J Microbiol Methods. 2003 May; 53(2):165-74, Schweitzer et al., Curr Opin Biotechnol. 2001 February; 12(1):21-7, U.S. Pat. Nos. 5,830,711, 6,027,889, 5,686,243, PCT Publication No. WO0056927A3, and PCT Publication No. WO9803673A1.

In some embodiments, amplification comprises at least one cycle of the sequential procedures of: annealing at least one primer with complementary or substantially complementary sequences in at least one target nucleic acid; synthesizing at least one strand of nucleotides in a template-dependent manner using a polymerase; and denaturing the newly-formed nucleic acid duplex to separate the strands. The cycle may or may not be repeated. Amplification can comprise thermocycling or can be performed isothermally.

As used herein, the term "amplification cross-hybridization" refers to hybridization of primers to non-target sequences within amplicons.

As used herein, a "flow cell attachment site" refers to a nucleotide sequence that can hybridize to a primer immobilized on a substrate, e.g., as in as the bridge amplification (cluster generation) and sequencing method commercialized by Illumina, Inc., San Diego, CA.

As used herein, the term "microfluidic device" refers to a device comprising multiple fluid flow paths, wherein each flow path has at least one, and often two, dimensions that are less than 1 millimeter.

As used with reference to a reaction, the term "multiplex" refers to the situation in which multiple such reactions are conducted simultaneously in a single reaction mixture. Thus, "multiplex amplification" refers to the simultaneous amplification of multiple target nucleic acids in a single reaction mixture.

As used herein with respect to reactions, reaction mixtures, reaction volumes, etc., the term "separate" refers to reactions, reaction mixtures, reaction volumes, etc., where reactions are carried out in isolation from other reactions. Separate reactions, reaction mixtures, reaction volumes, etc. include those carried out in droplets (See, e.g., U.S. Pat. No. 7,294,503, issued Nov. 13, 2007 to Quake et al., entitled "Microfabricated crossflow devices and methods," which is incorporated herein by reference in its entirety and specifically for its description of devices and methods for forming and analyzing droplets; U.S. Patent Publication No. 20100022414, published Jan. 28, 2010, by Link et al., entitled "Droplet libraries," which is incorporated herein by reference in its entirety and specifically for its description of devices and methods for forming and analyzing droplets; and U.S. Patent Publication No. 20110000560, published Jan. 6, 2011, by Miller et al., entitled "Manipulation of Microfluidic Droplets," which is incorporated herein by reference in its entirety and specifically for its description of devices and methods for forming and analyzing droplets.), which may, but need not, be in an emulsion, as well as those wherein reactions, reaction mixtures, reaction volumes, etc. are separated by mechanical barriers, e.g., separate vessels, separate wells of a microtiter plate, or separate chambers of a matrix-type microfluidic device.

A "single nucleotide polymorphism" (SNP) occurs at a polymorphic site occupied by a single nucleotide, which is the site of variation between allelic sequences. The site is usually preceded by and followed by highly conserved sequences of the allele (e.g., sequences that vary in less than 1/100 or 1/1000 members of the populations). A SNP usually arises due to substitution of one nucleotide for another at the polymorphic site. A transition is the replacement of one purine by another purine or one pyrimidine by another pyrimidine. A transversion is the replacement of a purine by a pyrimidine or vice versa. SNPs can also arise from a deletion of a nucleotide or an insertion of a nucleotide relative to a reference allele.

The designations "first" and "second" with respect to types of nucleotide sequences encompasses embodiments in which these types of nucleotide sequences are the same or different. In typical embodiments, however, these types of nucleotide sequences are different.

Amplification Methods—In General

Looping Amplification

The specificity of nucleic acid amplification can be increased by the use of "looping amplification" to reduce amplicon cross-hybridization. This increased specificity facilitates multiplexing to a much higher degree than was previously possible. In one embodiment, a looping amplification method is used to amplify one or more target nucleic acids. The method entails contacting sample nucleic acids with a novel forward primer pair for each target nucleic acid. The novel primer pair includes forward and reverse primers, wherein each primer comprises a target-specific portion and a common sequence 5' of the target-specific portion. The target nucleic acid(s) are amplified with the primer pair(s) to produce at least one target amplicon wherein a target nucleotide sequence is flanked by the common sequence on one end and its reverse complement on the other end. This configuration will tend to form a stem-loop structure. See FIG. 1. During annealing steps, the stem-loop structure will tend to form unless the appropriate target-specific primer is available to prime polymerization, which reduces amplicon cross-hybridization, as compared to when the amplification reaction is carried using standard primers that contain only target-specific sequences. In some embodiments, the average target amplicon size is greater (e.g., closer to the predicted amplicon size) than when amplification is carried out using primers containing only target-specific sequences.

Figure 8:
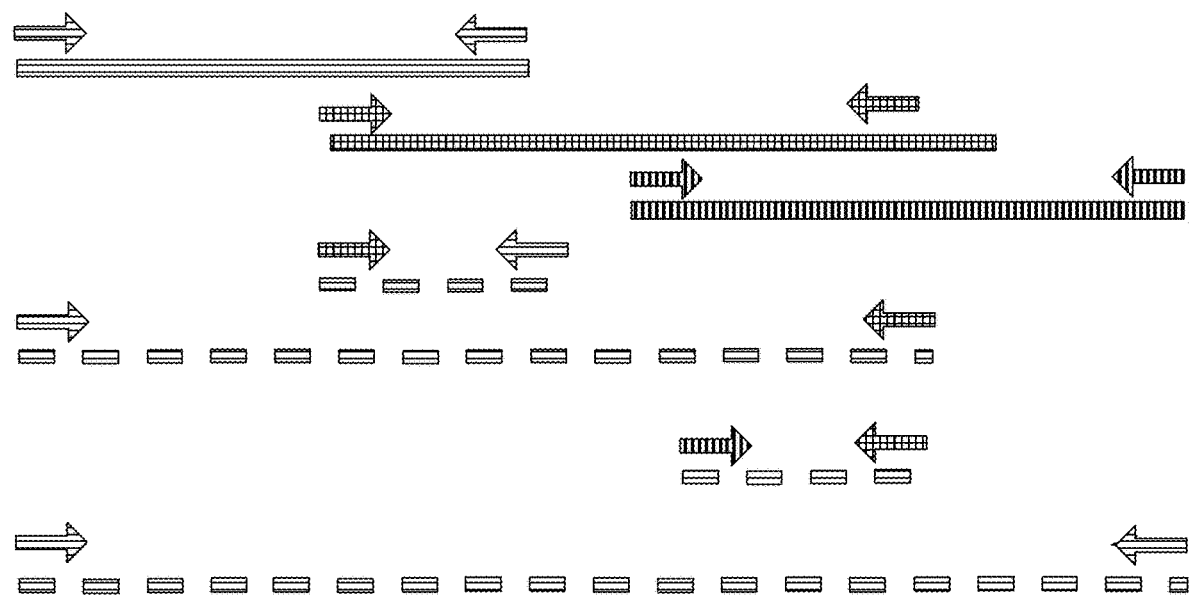
FIG. 8: Schematic illustration of "overlapped amplicons," in which three primer directed to the same general region of a sample nucleic acid can generate more than the expected three amplicons because a given forward primer can pair with multiple reverse primers.

This method can be used for high-specificity amplification of a single target nucleic acid in a reaction mixture or a plurality of target nucleic acids (e.g., 2, 3, 4, 5, 6, 7, 8, 9, or 10). The method particularly facilitates high-level multiplex amplification, e.g., wherein more than 10 target nucleic acids are amplified in a single reaction mixture. In various embodiments, at least 15, 20, 25, 30, 35, 40, 45, 50, 55, 60, 65, 70, 75, 80, 85, 90, 95, 100, 110, 120, 130, 140, 150, 160, 170, 180, 190, 200, 300, 400, 500, 600, 700, 800, 1000, 1500, 2000, 2500, 3000, 3500, 4000, 4500, 5000, 5500, or 6000, or more target nucleic acids are amplified in a single reaction mixture. In some embodiments, not more than 25,000, 20,000, 19,000, 18,000, 17,000, 16,000, 15,000, 14,000, 13,000, 12,000, 11,000, 10,000, 9000, 8000, 7000, 6000, 5000, 4000, 3000, 2000, 1000, 900, 800, 700, 600, 500, 450, 400, 350, 300, 250, 200, or 150 target nucleic acids are amplified in a single reaction mixture. The number of target nucleic acids amplified in a single reaction mixture can fall within any range bounded by any of the above values, e.g., 20-170, 40-160, 50-150, 60-140, 70-130, 80-120, 90-110, 100-25,000, 110-20,000, 120-19,000, 130-18,000, 140-17,000, 150-16,000, 160-15,000, 170-14,000, 180-13,000, 190-12,000, 200-1100. In some embodiments, the highest levels of multiplexing results from "overlapped amplicons." Overlapped amplicons are generated when multiple primer pairs are directed to the same general region of a sample nucleic acid. In this case, a forward primer from a given primer pair can produce an amplicon from the reverse primer in the pair, but can also produce amplicons from other reverse primers. This phenomenon is shown schematically in FIG. 8.

The common sequence can be any sequence and must be sufficiently long to form a stem, i.e., at least 2 nucleotides, and more typically at least 3, 4, 5, 6, 7, 8, 9, 10, 11, 12, 13, 14, 15, 16, 17, 18, 19, 20, 21, 22, 23, 14, 25, 26, 27, 28, 29, 30, 31, 32, 33, 34, 35, 36, 37, 38, 39, or 40 nucleotides. In some embodiments, the stem is not more than 100, 80, 70, 60, 50, 40, 30, or 20 nucleotides. The length of the stem can fall within any range bounded by any of the above values, e.g., 5-45, 8-40, 10-35, 13-30, 15-25, or 18-20 nucleotides.

In particular embodiments, the common sequence is one that facilitates downstream analysis of the target amplicon, such as, for example, by DNA sequencing. In this case, looping amplification can be used to introduce sequences flanking the target nucleotide sequence that facilitate DNA sequencing (e.g., DNA sequencing adaptors).

Looping amplification can, for example, by used to prepare DNA sequencing templates that are compatible with Illumina's bridge PCR system. Illumina-compatible libraries are conventionally prepared by tagmentation (NEXTERA™ DNA Sample Prep Kit), which uses transposons to simultaneously fragment and add nucleotide tags which serve as binding sites for DNA sequencing primers and are also used to add flow cell attachment sites. Because the resultant templates contain transposon sequences, the common sequence for looping amplification can be a suitable transposon sequence, e.g., 5'-AGATGTGTNNNAGA-GACAG-3' (SEQ ID NO:1). Table 1 below shows all possible nucleotide sequences for the NNN sequence in SEQ ID NO:1.

TABLE 1

| First N | Second N | Third N |
|---------|----------|---------|
| A | A | A |
| " | " | T |
| " | " | G |
| " | " | C |
| " | T | A |
| " | " | T |
| " | " | G |
| " | " | C |
| " | G | A |
| " | " | T |
| " | " | G |
| " | " | C |
| " | C | A |
| " | " | T |
| " | " | G |

TABLE 1-continued

| First N | Second N | Third N |
| --- | --- | --- |
| " | " | C |
| T | A | A |
| " | " | T |
| " | " | G |
| " | " | C |
| " | T | A |
| " | " | T |
| " | " | G |
| " | " | C |
| " | G | A |
| " | " | T |
| " | " | G |
| " | " | C |
| " | C | A |
| " | " | T |
| " | " | G |
| " | " | C |
| G | A | A |
| " | " | T |
| " | " | G |
| " | " | C |
| " | T | A |
| " | " | T |
| " | " | G |
| " | " | C |
| " | G | A |
| " | " | T |
| " | " | G |
| " | " | C |
| " | C | A |
| " | " | T |
| " | " | G |
| " | " | C |
| C | A | A |
| " | " | T |
| " | " | G |
| " | " | C |
| " | T | A |
| " | " | T |
| " | " | G |
| " | " | C |
| " | G | A |
| " | " | T |
| " | " | G |
| " | " | C |
| " | C | A |
| " | " | T |
| " | " | G |
| " | " | C |

" indicates the same nucleotide as above.

In a specific embodiment, the common sequence is the transposon sequence used in the NEXTERA™ DNA Sample Prep Kit, which is 5'-AGATGTGTATAAGAGACAG-3' (SEQ ID NO:2).

In certain embodiments, the forward primer and/or the reverse primer for each target nucleic acid include(s) a tag nucleotide sequence 5' of the common sequence. In particular embodiments, both primers include tag nucleotide sequences, and the tag nucleotide sequence in the forward primer is different from the tag nucleotide sequence in the reverse primer. The different tags can be used to add different sequences to either end of the target amplicon, e.g., the two different flow cell attachment sites used in Illumina's bridge sequencing system.

Figure 2:
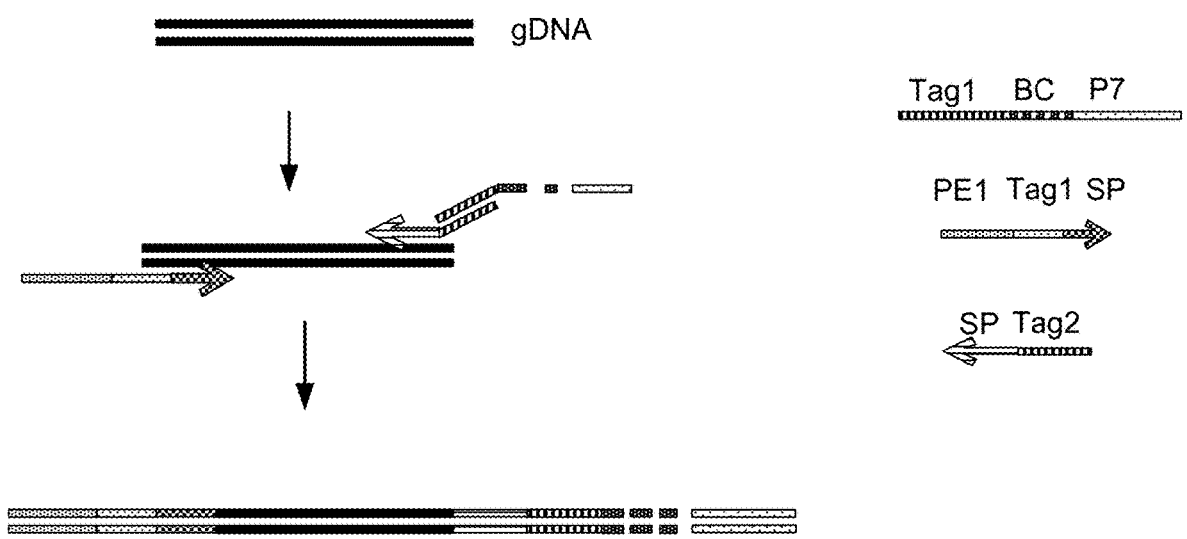
FIG. 2: 1-step, 3-primer PCR barcoding scheme for use in a matrix-type microfluidic device.

To facilitate sequencing the forward and/or reverse primers can include an additional nucleotide sequence 3' of the tag sequence, which can be, for example, a binding site for a DNA sequencing primer. In an illustrative embodiment, a forward primer can contain: 5'-first tag nucleotide sequence-first binding site for a first DNA sequencing primer-common sequence-first target-specific sequence-3', and a reverse primer can contain: 5'-second tag nucleotide sequence-second binding site for a second DNA sequencing primer-common sequence-second target-specific sequence. Illustrative forward and reverse primers of this type are shown in FIG. 2, where the DNA sequencing primer binding sites are indicated as "SP," and their positions relative to "Tag1" and "Tag2" are shown (the target-specific and common sequences are not shown).

Looping Amplification with 1-Step Addition of Sequences for DNA Sequencing

One approach to using looping amplification for preparing templates for bridge sequencing is a 1-step, 3-primer method. See FIG. 2. In this method, either the forward or reverse primer described above for use in sequencing additionally includes a first flow cell attachment site 5' of the tag nucleotide sequence. For sequencing on the Illumina system, this first flow cell attachment site can be PE1, as shown in FIG. 2. Amplification can be carried out using a third primer in addition to the forward and reverse primer, to add a second additional nucleotide sequence. All primers are present in one amplification mixture, and all desired sequences are added in one (multi-cycle) amplification step. In this case, the third primer includes a tag-specific portion, with the second additional nucleotide sequence 5' of the tag-specific portion. For 1-step amplification, the third primer is typically included in the amplification mixture at at least 5-fold the concentration of the forward and reverse primers. The second additional nucleotide sequence can include an optional barcode nucleotide sequence, which, if present, is 5' of the tag-specific portion. For bridge sequencing, the second additional nucleotide sequence includes a 5' second flow cell attachment site. FIG. 2 shows an illustrative third primer having a 5' P7 sequence as the second flow cell attachment site, which is separated from the tag-specific portion (Tag1) by a barcode nucleotide sequence ("BC"). As shown in FIG. 2, if the first flow cell attachment site is part of the forward primer, the third primer is specific for the tag on the reverse primer. Conversely, if the first flow cell attachment site is part of the reverse primer, the third primer is specific for the tag on the forward primer.

Looping Amplification with 2-Step Addition of Sequences for DNA Sequencing

Figure 3:
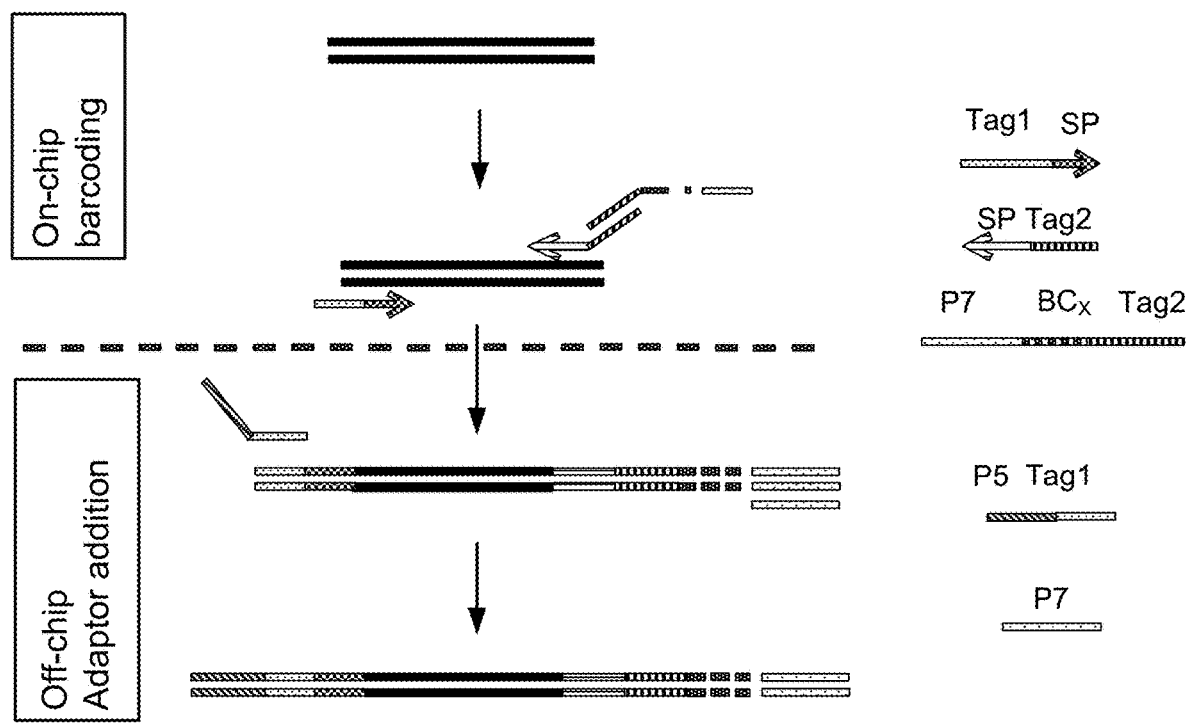
FIG. 3: 2-step PCR barcoding scheme with 3-primer barcoding on chip in a matrix-type microfluidic device ("on-chip"), and 1-tube PCR to add sequencing adaptors ("off-chip").

Another approach to using looping amplification for preparing templates for bridge sequencing is a 2-step method, where the first step employs 3 primers, and the second step employs 2 primers. See FIG. 3. Typically, these steps are carried out in separate amplification mixtures. In particular embodiments, the first step is carried out using the forward and reverse primers described above for use in sequencing, e.g.: a forward primer containing: 5'-first tag nucleotide sequence-first binding site for a first DNA sequencing primer-common sequence-first target-specific sequence-3', and a reverse primer containing: 5'-second tag nucleotide sequence-second binding site for a second DNA sequencing primer-common sequence-second target-specific sequence. These forward and reverse primers are shown in FIG. 3 as "Tag1 SP" and "SP Tag2." The first step also includes a third primer, wherein the third primer comprises a tag-specific portion, a barcode nucleotide sequence 5' of the tag-specific portion, and a second flow cell attachment site 5' of the barcode nucleotide sequence. For sequencing on the Illumina system, this second flow cell attachment site can be PE7, as shown in FIG. 3, where this third primer is indicated as "P7 BCx Tag2." The first amplification step using these three primers produces target amplicons having the structure: 5'-first nucleotide tag-first primer binding site-common sequence-target nucleotide sequence-reverse complement of common sequence-second primer binding site-second nucleotide tag-barcode nucleotide sequence-second flow cell attachment site-3'.

In some embodiments, the 1-step method described above or the first step of the 2-step method can be carried out in a plurality of separate reaction mixtures. Each separate reaction mixture can contain one or more primer sets suitable for amplifying one or more target nucleic acids. To increase throughput, amplification is carried in multiplex (i.e., with primers for multiple targets in each reaction mixture). As discussed above, looping amplification permits high-level multiplexing, which is particularly useful, in the DNA sequencing context, for targeted re-sequencing.

The reaction mixtures can be formed in any way, for example as droplets (e.g., in an emulsion) or within chambers in a microfluidic device. Microfluidic devices useful in the methods described herein are discussed in greater detail below. For high-throughput analyses, microfluidic devices having a plurality of reaction chambers can be used. Matrix-type microfluidic devices are convenient for this purpose, especially when multiple targets are to be analyzed in different samples in one experiment. Matrix-type devices permit samples to be loaded into the device in one dimension (i.e., columns or rows), while primers can be loaded into the device in the other dimension (i.e., rows or columns, respectively). If different samples are loaded into columns and different primers are loaded into rows, a plurality of target nucleic acids can be amplified in each of a plurality of reaction chambers in the device by loading multiple primer sets into each row. In this case, the number of simultaneous amplifications that can be carried out in the device is the number of reaction chambers×the number of primer sets in each reaction chamber. If, for example, the microfluidic device contains 48 columns for 48 different samples and 48 separate rows, and looping amplification is used to amplify more than 10 target nucleic acids in each chamber, 480 target nucleic acids can be amplified for each sample. If looping amplification is used to amplify at least 100 target nucleic acids in each chamber, at least 4800 target nucleic acids can be amplified for each sample.

Where the amplification is carried out to prepare templates for DNA sequencing and the 2-step method described above is used, the reaction products ("target amplicons") from the first amplification are recovered and subjected to a second amplification step with two different primers. If the first step is performed in a microfluidic device, the target amplicons can be recovered and subjected to the second amplification step outside of a microfluidic device or in a different microfluidic device. Thus, FIG. 3 refers to "On-chip barcoding" for the first step and "Off-chip Adaptor addition" for the second step. The on-chip portion of this method is conveniently carried out using Fluidigm Corporation's ACCESS ARRAY™ IFC (Integrated Fluidic Circuit), for example.

As shown in FIG. 3, in some embodiments, it is advantageous to add at least one further nucleotide sequence to each of the target amplicons produced from the first amplification step. When bridge sequencing is to be performed, the further nucleotide sequence can be the first flow cell attachment site, the second flow cell attachment site having been added in the first amplification step. The first flow cell attachment site is added to the end of the amplicon opposite the second flow cell attachment site. In the description above, since the second flow cell attachment site was introduced at the "reverse primer" end of the amplicon, the forward primer for the second amplification step has a portion specific for the first nucleotide tag and a first flow cell attachment site 5' of said tag-specific portion. This forward primer is shown as "P5 Tag1" in FIG. 3. The reverse primer for the second amplification step is specific for the second flow cell attachment site ("P7" in FIG. 3).

The result of either the 1-step or 2-step methods for adding sequences for DNA sequencing is, in some embodiments, a DNA sequencing library, wherein each member of the library has the structure: 5'-first flow cell attachment site-first nucleotide tag-first primer binding site-common sequence-target nucleotide sequence-reverse complement of common sequence-second primer binding site-second nucleotide tag-barcode nucleotide sequence-second flow cell attachment site-3'.

In some embodiments, an additional barcode nucleotide sequence is added to each target amplicon. For example, an additional barcode nucleotide sequence may be introduced at the end of the target amplicon opposite the end bearing the barcode nucleotide sequence discussed above (and shown in FIG. 3 as BCx). When adding sequences for DNA sequencing, each member of the DNA sequencing library can have the structure: 5'-first flow cell attachment site-first barcode nucleotide sequence-first nucleotide tag-first primer binding site-common sequence-target nucleotide sequence-reverse complement of common sequence-second primer binding site-second nucleotide tag-second barcode nucleotide sequence-second flow cell attachment site-3'. In the scheme of FIG. 3, this structure could be produced, for example, by including a first barcode nucleotide sequence (not shown) in the forward primer is shown as "P5 Tag1" in the Off-chip Adapter addition. The "second" barcode nucleotide sequence (identified as BCx) would have already been incorporated into the target amplicons in the On-chip barcoding step.

The primer concentration of the first step of the two-step looping amplification protocol can be adjusted, depending on whether amplicon overlapping, and thus a greater number of possible primer pairs, is desired. This might be the case, for example, when the aim is to sequence a particular region of a sample nucleic acid. Example 4 shows that a primer concentration of 2 nM for the first step gives a major band in the expected amplicon size range for non-overlapped amplicons. Reducing this concentration to 1 nM allows for greater amplicon overlapping, and a further reduction to 0.5 nM allows for even more amplicon overlapping which yields multiple bands over a much boarder range of amplicon sizes. Also, reduction of primer concentration in looping amplification promotes amplification specificity.

Sample Nucleic Acids

Preparations of nucleic acids ("samples") can be obtained from biological sources and prepared using conventional methods known in the art. In particular, DNA or RNA useful in the methods described herein can be extracted and/or amplified from any source, including bacteria, protozoa, fungi, viruses, organelles, as well higher organisms such as plants or animals, particularly mammals, and more particularly humans. Suitable nucleic acids can also be obtained from environmental sources (e.g., pond water), from man-made products (e.g., food), from forensic samples, and the like. Nucleic acids can be extracted or amplified from cells, bodily fluids (e.g., blood, a blood fraction, urine, etc.), or tissue samples by any of a variety of standard techniques. Illustrative samples include samples of plasma, serum, spinal fluid, lymph fluid, peritoneal fluid, pleural fluid, oral fluid, and external sections of the skin; samples from the respiratory, intestinal genital, and urinary tracts; samples of tears, saliva, blood cells, stem cells, or tumors. For example, samples of fetal DNA can be obtained from an embryo or from maternal blood. Samples can be obtained from live or dead organisms or from in vitro cultures. Illustrative samples can include single cells, formalin-fixed and/or paraffin-embedded tissue samples, and needle biopsies. Nucleic acids useful in the methods described herein can also be derived from one or more nucleic acid libraries, including cDNA, cosmid, YAC, BAC, P1, PAC libraries, and the like.

Nucleic acids of interest can be isolated using methods well known in the art, with the choice of a specific method depending on the source, the nature of nucleic acid, and similar factors. The sample nucleic acids need not be in pure form, but are typically sufficiently pure to allow the reactions of interest to be performed. Where the target nucleic acids are RNA, the RNA can be reversed transcribed into cDNA by standard methods known in the art and as described in Sambrook, J., Fritsch, E. F., and Maniatis, T., *Molecular Cloning: A Laboratory Manual*. Cold Spring Harbor Laboratory Press, NY, Vol. 1, 2, 3 (1989), for example.

Target Nucleic Acids

Target nucleic acids useful in the methods described herein can be derived from any of the sample nucleic acids described above. In typical embodiments, at least some nucleotide sequence information will be known for the target nucleic acids. For example, if PCR is employed as the amplification reaction, sufficient sequence information is generally available for each end of a given target nucleic acid to permit design of suitable amplification primers. In an alternative embodiment, target-specific sequences in primers could be replaced by random or degenerate nucleotide sequences.

The targets can include, for example, nucleic acids associated with pathogens, such as viruses, bacteria, protozoa, or fungi; RNAs, e.g., those for which over- or under-expression is indicative of disease, those that are expressed in a tissue- or developmental-specific manner; or those that are induced by particular stimuli; genomic DNA, which can be analyzed for specific polymorphisms (such as SNPs), alleles, or haplotypes, e.g., in genotyping. Of particular interest are genomic DNAs that are altered (e.g., amplified, deleted, rearranged, and/or mutated) in genetic diseases or other pathologies; sequences that are associated with desirable or undesirable traits; and/or sequences that uniquely identify an individual (e.g., in forensic or paternity determinations). When multiple target nucleic acids are employed, these can be on the same or different chromosome(s).

In various embodiments, a target nucleic acid to be amplified can be, e.g., 25 bases, 50 bases, 100 bases, 200 bases, 500 bases, or 750 bases. In certain embodiments of the methods described herein, a long-range amplification method, such as long-range PCR can be employed to produce amplicons from the amplification mixtures. Long-range PCR permits the amplification of target nucleic acids ranging from one or a few kilobases (kb) to over 50 kb. In various embodiments, the target nucleic acids that are amplified by long-range PCR are at least about 1, 2, 3, 4, 5, 6, 7, 8, 9, 10, 11, 12, 13, 14, 15, 20, 25, 30, 35, 40, 45, or 50 kb in length. Target nucleic acids can also fall within any range having any of these values as endpoints (e.g., 25 bases to 100 bases or 5-15 kb).

Primer Design

Primers suitable for nucleic acid amplification are sufficiently long to prime the synthesis of extension products in the presence of the agent for polymerization. The exact length and composition of the primer will depend on many factors, including, for example, temperature of the annealing reaction, source and composition of the primer. For example, depending on the complexity of the target nucleic acid sequence, an oligonucleotide primer typically contains in the range of about 15 to about 30 nucleotides, although it may contain more or fewer nucleotides. The primers should be sufficiently complementary to selectively anneal to their respective strands and form stable duplexes. One skilled in the art knows how to select appropriate primer pairs to amplify the target nucleic acid of interest. For example, PCR primers can be designed by using any commercially available software or open source software, such as Primer3 (see, e.g., Rozen and Skaletsky (2000) *Meth. Mol. Biol.,* 132: 365-386; www.broad.mit.edu/node/1060, and the like) or by accessing the Roche UPL website.

Primers may be prepared by any suitable method, including, for example, cloning and restriction of appropriate sequences or direct chemical synthesis by methods such as the phosphotriester method of Narang et al. (1979) *Meth. Enzymol.* 68: 90-99; the phosphodiester method of Brown et al. (1979) *Meth. Enzymol.* 68: 109-151; the diethylphosphoramidite method of Beaucage et al. (1981) *Tetra. Lett.,* 22: 1859-1862; the solid support method of U.S. Pat. No. 4,458,066 and the like, or can be provided from a commercial source.

Primers may be purified by using a Sephadex column (Amersham Biosciences, Inc., Piscataway, NJ) or other methods known to those skilled in the art. Primer purification may improve the sensitivity of the methods described herein.

Amplification

Nucleic acids can be amplified in accordance with the methods described herein for any useful purpose, e.g., to detect and/or quantify and/or sequence one or more target nucleic acids. Amplification can be carried out in droplets, in emulsions, in vessels, in wells of a microtiter plate, in chambers of a matrix-type microfluidic device, etc.

In certain embodiments, amplification methods are employed to produce amplicons suitable for automated DNA sequencing. Many current DNA sequencing techniques rely on "sequencing by synthesis." These techniques entail library creation, massively parallel PCR amplification of library molecules, and sequencing. Conventionally, library creation starts with conversion of sample nucleic acids to appropriately sized fragments, ligation of adaptor sequences onto the ends of the fragments, and selection for molecules properly appended with adaptors. The presence of the adaptor sequences on the ends of the library molecules enables amplification of random-sequence inserts. The above-described methods for tagging target nucleotide sequences can be substituted for ligation, to incorporate adaptor sequences.

The above-described methods provide substantially uniform amplification of target nucleotide sequences, which is helpful in preparing DNA sequencing libraries having good coverage. In the context of automated DNA sequencing, the term "coverage" refers to the number of times the sequence is measured upon sequencing. A DNA sequencing library that has substantially uniform coverage can yield sequence data where the coverage is also substantially uniform. Thus, in various embodiments, upon performing automated sequencing of a plurality of target amplicons prepared as described herein, the sequences of at least 50 percent of the target amplicons are present at greater than 50 percent of the average number of copies of target amplicon sequences and less than 2-fold the average number of copies of target amplicon sequences. In various embodiments of this method at least 55, at least 60, at least 65, at least 70, at least 75, at least 80, at least 85, at least 90, at least 91, at least 92, at least 93, at least 94, at least 95, at least 96, at least 97, at least 98, or at least 99 percent of the target amplicon sequences are present at greater than 50 percent of the average number of copies of target amplicon sequences and less than 2-fold the average number of copies of target amplicon sequences.

The methods described herein can include subjecting at least one target amplicon to DNA sequencing using any available DNA sequencing method. In particular embodiments, a plurality of target amplicons is sequenced using a high throughput sequencing method. Such methods typically use an in vitro cloning step to amplify individual DNA molecules. For example, emulsion PCR (emPCR) isolates individual DNA molecules along with primer-coated beads in aqueous droplets within an oil phase. PCR produces copies of the DNA molecule, which bind to primers on the bead, followed by immobilization for later sequencing. In vitro clonal amplification can also be carried out by "bridge PCR," where fragments are amplified upon primers attached to a solid surface. DNA molecules that are physically bound to a surface can be sequenced in parallel, for example, by a pyrosequencing or sequencing-by-synthesis method.

Microfluidic Devices

In certain embodiments, methods described herein can be carried out using a microfluidic device. In illustrative embodiments, the device is a matrix-type microfluidic device that allows the simultaneous combination of a plurality of substrate solutions with reagent solutions in separate isolated reaction chambers. It will be recognized, that a substrate solution can include one or a plurality of substrates (e.g., target nucleic acids) and a reagent solution can include one or a plurality of reagents (e.g., amplification primers). For example, the microfluidic device can allow the simultaneous pair-wise combination of a plurality of different samples and amplification primers. In certain embodiments, the device is configured to contain a different combination of primers and samples in each of the different chambers. In various embodiments, the number of separate reaction chambers can be greater than 50, usually greater than 100, more often greater than 500, even more often greater than 1000, and sometimes greater than 5000, or greater than 10,000.

In particular embodiments, the matrix-type microfluidic device is a DYNAMIC ARRAY™ IFC ("DA") microfluidic device. A DA microfluidic device is a matrix-type microfluidic device designed to isolate pair-wise combinations of samples and reagents (e.g., amplification primers, detection probes, etc.) and suited for carrying out qualitative and quantitative PCR reactions including real-time quantitative PCR analysis. In some embodiments, the DA microfluidic device is fabricated, at least in part, from an elastomer. DA microfluidic devices are described in PCT Publication No. WO05107938A2 (Thermal Reaction Device and Method For Using The Same) and U.S. Patent Publication No. US20050252773A1, both incorporated herein by reference in their entireties for their descriptions of DA microfluidic devices. DA microfluidic devices may incorporate high-density matrix designs that utilize fluid communication vias between layers of the microfluidic device to weave control lines and fluid lines through the device and between layers. By virtue of fluid lines in multiple layers of an elastomeric block, high density reaction cell arrangements are possible. Alternatively DA microfluidic devices may be designed so that all of the reagent and sample channels are in the same elastomeric layer, with control channels in a different layer. In certain embodiments, DA microfluidic devices may be used for reacting M number of different samples with N number of different reagents.

Although the DA microfluidic devices described in WO05107938 are well suited for conducting the methods described herein, the invention is not limited to any particular device or design. Any device that partitions a sample and/or allows independent pair-wise combinations of reagents and sample may be used. U.S. Patent Publication No. 20080108063 (which is hereby incorporated by reference it its entirety) includes a diagram illustrating the 48.48 DYNAMIC ARRAY™ IFC, a commercially available device available from Fluidigm Corp. (South San Francisco Calif). It will be understood that other configurations are possible and contemplated such as, for example, 48×96; 96×96; 30×120; etc.

In specific embodiments, the microfluidic device can be a DIGITAL ARRAY™ IFC microfluidic device, which is adapted to perform digital amplification. Such devices can have integrated channels and valves that partition mixtures of sample and reagents into nanolitre volume reaction chambers. In some embodiments, the DIGITAL ARRAY™ IFC microfluidic device is fabricated, at least in part, from an elastomer. Illustrative DIGITAL ARRAY™ IFC microfluidic devices are described in copending U.S. Applications owned by Fluidigm Corp. (South San Francisco, CA), such as U.S. application Ser. No. 12/170,414, entitled "Method and Apparatus for Determining Copy Number Variation Using Digital PCR." One illustrative embodiment has 12 input ports corresponding to 12 separate sample inputs to the device. The device can have 12 panels, and each of the 12 panels can contain 765 6 nL reaction chambers with a total volume of 4.59 µL per panel. Microfluidic channels can connect the various reaction chambers on the panels to fluid sources. Pressure can be applied to an accumulator in order to open and close valves connecting the reaction chambers to fluid sources. In illustrative embodiments, 12 inlets can be provided for loading of the sample reagent mixture. 48 inlets can be used to provide a source for reagents, which are supplied to the chip when pressure is applied to accumulator. Additionally, two or more inlets can be provided to provide hydration to the chip.

While the DIGITAL ARRAY™ IFC microfluidic devices are well suited for carrying out certain amplification methods described herein, one of ordinary skill in the art would recognize many variations and alternatives to these devices. The geometry of a given DIGITAL ARRAY™ IFC microfluidic device will depend on the particular application. Additional description related to devices suitable for use in the methods described herein is provided in U.S. Patent Publication No. 20050252773, incorporated herein by reference for its disclosure of DIGITAL ARRAY™ IFC microfluidic devices.

In certain embodiments, the methods described herein can be performed using a microfluidic device that provides for recovery of reaction products. Such devices are described in detail in U.S. Pat. No. 8,691,509, (which is hereby incorporated by reference in its entirety and specifically for its description of microfluidic devices that permit reaction product recovery and related methods) and sold by Fluidigm Corp. as ACCESS ARRAY™ IFC (Integrated Fluidic Circuit).

In an illustrative device of this type, independent sample inputs are combined with primer inputs in an M×N array configuration. Thus, each reaction is a unique combination of a particular sample and a particular reagent mixture. Samples are loaded into sample chambers in the microfluidic device through sample input lines arranged as columns in one implementation. Assay reagents (e.g., primers) are loaded into assay chambers in the microfluidic device through assay input lines arranged as rows crossing the columns. The sample chambers and the assay chambers are in fluidic isolation during loading. After the loading process is completed, an interface valve operable to obstruct a fluid line passing between pairs of sample and assay chambers is opened to enable free interface diffusion of the pairwise combinations of samples and assays. Precise mixture of the samples and assays enables reactions to occur between the various pairwise combinations, producing one or more reaction product(s) in each chamber. The reaction products are harvested and can then be used for subsequent processes. The terms "assay" and "sample" as used herein are descriptive of particular uses of the devices in some embodiments. However, the uses of the devices are not limited to the use of "sample(s)" and "assay(s)" in all embodiments. For example, in other embodiments, "sample(s)" may refer to "a first reagent" or a plurality of "first reagents" and "assay(s)" may refer to "a second reagent" or a plurality of "second reagents." The M×N character of the devices enable the combination of any set of first reagents to be combined with any set of second reagents.

According to particular embodiments, the reaction products from the M×N pairwise combinations can be recovered from the microfluidic device in discrete pools, e.g., one for each of M samples. Typically, the discrete pools are contained in a sample input port provided on the carrier. In some processes, the reaction products may be harvested on a "per amplicon" basis for purposes of normalization. Utilizing embodiments of the present invention, it is possible to achieve results (for replicate experiments assembled from the same input solutions of samples and assays) for which the copy number of amplification products varies by no more than ±25% within a sample and no more than ±25% between samples. Thus, the amplification products recovered from the microfluidic device will be representative of the input samples as measured by the distribution of specific known genotypes. In certain embodiments, output sample concentration will be greater than 2,000 copies/amplicon/microliter, and recovery of reaction products will be performed in less than two hours.

In some embodiments, reaction products are recovered by dilation pumping. Dilation pumping provides benefits not typically available using conventional techniques. For example, dilation pumping enables for a slow removal of the reaction products from the microfluidic device. In an exemplary embodiment, the reaction products are recovered at a fluid flow rate of less than 100 µl per hour. In this example, for 48 reaction products distributed among the reaction chambers in each column, with a volume of each reaction product of about 1.5 µl, removal of the reaction products in a period of about 30 minutes, will result in a fluid flow rate of 72 µl/hour. (i.e., 48×1.5/0.5 hour). In other embodiments, the removal rate of the reaction products is performed at a rate of less than 90 µl/hr, 80 µl/hr, 70 µl/hr, 60 µl/hr, 50 µl/hr, 40 µl/hr, 30 µl/hr, 20 µl/hr, 10 µl/hr, 9 µl/hr, less than 8 µl/hr, less than 7 µl/hr, less than 6 µl/hr, less than 5 µl/hr, less than 4 µl/hr, less than 3 µl/hr, less than 2 µl/hr, less than 1 µl/hr, or less than 0.5 µl/hr.

Dilation pumping results in clearing of substantially a high percentage and potentially all the reaction products present in the microfluidic device. Some embodiments remove more than 75% of the reaction products present in the reaction chambers (e.g., sample chambers) of the microfluidic device. As an example, some embodiments remove more than 80%, 85%, 90%, 92%, 95%, 96%, 97%, 98%, or 99% of the reaction products present in the reaction chambers.

The methods described herein may use microfluidic devices with a plurality of "unit cells" that generally include a sample chamber and an assay chamber. Such unit cells can have dimensions on the order of several hundred microns, for example unit cells with dimension of 500×500 µm, 525×525 µm, 550×550 µm, 575×575 µm, 600×600 µm, 625×625 µm, 650×650 µm, 675×675 µm, 700×700 µm, or the like. The dimensions of the sample chambers and the assay chambers are selected to provide amounts of materials sufficient for desired processes while reducing sample and assay usage. As examples, sample chambers can have dimensions on the order of 100-400 µm in width×200-600 µm in length×100-500 µm in height. For example, the width can be 100 µm, 125 µm, 150 µm, 175 µm, 200 µm, 225 µm, 250 µm, 275 µm, 300 µm, 325 µm, 350 µm, 375 µm, 400 µm, or the like. For example, the length can be 200 µm, 225 µm, 250 µm, 275 µm, 300 µm, 325 µm, 350 µm, 375 µm, 400 µm, 425 µm, 450 µm, 475 µm, 500 µm, 525 µm, 550 µm, 575 µm, 600 µm, or the like. For example, the height can be 100 µm, 125 µm, 150 µm, 175 µm, 200 µm, 225 µm, 250 µm, 275 µm, 300 µm, 325 µm, 350 µm, 375 µm, 400 µm, 425 µm, 450 µm, 475 µm, 500 µm, 525 µm, 550 µm, 575 µm, 600 µm, or the like. Assay chambers can have similar dimensional ranges, typically providing similar steps sizes over smaller ranges than the smaller chamber volumes. In some embodiments, the ratio of the sample chamber volume to the assay chamber volume is about 5:1, 10:1, 15:1, 20:1, 25:1, or 30:1. Smaller chamber volumes than the listed ranges are included within the scope of the invention and are readily fabricated using microfluidic device fabrication techniques.

Higher density microfluidic devices will typically utilize smaller chamber volumes in order to reduce the footprint of the unit cells. In applications for which very small sample sizes are available, reduced chamber volumes will facilitate testing of such small samples.

For single-particle analysis, microfluidic devices can be designed to facilitate loading and capture of the particular particles to be analyzed. Each unit cell has a "cell channel" (i.e., sample chamber) and an "assay channel" (i.e., assay chamber). The cell channel is rounded for loading mammalian cells, with dimensions on the order of tens microns in diameter to a hundred of several hundred microns in length. Diameters can be about 15 µm, about 20 µm, about 25 µm, about 30 µm, about 35 µm, about 40 µm, or about 45 µm or more, or can fall within a range having any of these values as endpoints, depending on the size of the cells being analyzed. Lengths can be about 60 µm, about 90 µm, about 120 µm, about 150 µm, about 170 µm, about 200 µm, about 230 µm, about 260 µm, about 290 µm or more, or can fall within a range having any of these values as endpoints, depending on the size of the cells being analyzed. In an illustrative microfluidic device based on the ACCESS ARRAY™ IFC platform (the "MA006"), a unit cell for loading mammalian cells can be about 30 µm×170 µm. Such a device can be equipped to provide, or to facilitate providing, heat to cell channels after loading to lyse the cells. The device can include assay channels separate from cell channels for conducting reactions such as nucleic acid amplification. 170 µm×170 containment valves can be used to close cell channels.

U.S. App. No. 61/605,016, filed Feb. 29, 2012, and entitled "Methods, Systems, And Devices For Multiple Single-Particle or Single-Cell Processing Using Microfluidics," describes methods, systems, and devices for multiple single-particle or single-cell processing utilizing microfluidics. Various embodiments provide for capturing, partitioning, and/or manipulating individual particles or cells from a larger population of particles of cells along with generating genetic information and/or reaction(s) related to each individual particle or cell. Some embodiments may be configured for imaging the individual particles or cells or associated reaction products as part of the processing. This application is incorporated by reference herein it its entirety and, in particular, for its description of microfluidic devices configured for multiple single-particle or single-cell processing and related systems.

Fabrication methods using elastomeric materials and methods for design of devices and their components have been described in detail in the scientific and patent literature. See, e.g., Unger et al. (2000) Science 288:113-116; U.S. Pat. Nos. U.S. Pat. No. 6,960,437 (Nucleic acid amplification utilizing microfluidic devices); U.S. Pat. No. 6,899,137 (Microfabricated elastomeric valve and pump systems); U.S. Pat. No. 6,767,706 (Integrated active flux microfluidic devices and methods); U.S. U.S. Pat. No. 6,752,922 (Microfluidic chromatography); U.S. Pat. No. 6,408,878 (Microfabricated elastomeric valve and pump systems); U.S. Pat. No. 6,645,432 (Microfluidic devices including three-dimensionally arrayed channel networks); U.S. Patent Application Publication Nos. 2004/0115838; 2005/0072946; 2005/0000900; 2002/0127736; 2002/0109114; 2004/0115838; 2003/0138829; 2002/0164816; 2002/0127736; and 2002/0109114; PCT Publication Nos. WO 2005/084191; WO 05/030822A2; and WO 01/01025; Quake & Scherer, 2000, "From micro to nanofabrication with soft materials" Science 290: 1536-40; Unger et al., 2000, "Monolithic microfabricated valves and pumps by multilayer soft lithography" Science 288:113-116; Thorsen et al., 2002, "Microfluidic large-scale integration" Science 298:580-584; Chou et al., 2000, "Microfabricated Rotary Pump" Biomedical Microdevices 3:323-330; Liu et al., 2003, "Solving the "world-to-chip" interface problem with a microfluidic matrix" Analytical Chemistry 75, 4718-23, Hong et al, 2004, "A nanoliter-scale nucleic acid processor with parallel architecture" Nature Biotechnology 22:435-39.

Applications

In particular embodiments, the methods described herein are used in the analysis of one or more nucleic acids, e.g. (in some embodiments). Thus, for example, these methods are applicable to identifying the presence of particular polymorphisms (such as SNPs), alleles, or haplotypes, or chromosomal abnormalities, such as amplifications, deletions, rearrangements, or aneuploidy. The methods may be employed in genotyping or sequencing, which can be carried out in a number of contexts, including diagnosis of genetic diseases or disorders, cancer, pharmacogenomics (personalized medicine), quality control in agriculture (e.g., for seeds or livestock), the study and management of populations of plants or animals (e.g., in aquaculture or fisheries management or in the determination of population diversity), or paternity or forensic identifications. The methods described herein can be applied in the identification of sequences indicative of particular conditions or organisms in biological or environmental samples. For example, the methods can be used in assays to identify pathogens, such as viruses, bacteria, and fungi. The methods can also be used in studies aimed at characterizing environments or microenvironments, e.g., characterizing the microbial species in the human gut.

In certain embodiments, these methods can also be employed in determinations of DNA or RNA copy number. Determinations of aberrant DNA copy number in genomic DNA is useful, for example, in the diagnosis and/or prognosis of genetic defects and diseases, such as cancer. Determination of RNA "copy number," i.e., expression level is useful for expression monitoring of genes of interest, e.g., in different individuals, tissues, or cells under different conditions (e.g., different external stimuli or disease states) and/or at different developmental stages.

In addition, the methods can be employed to prepare nucleic acid samples for further analysis, such as, e.g., DNA sequencing.

Furthermore, nucleic acid samples can be tagged as a first step, prior subsequent analysis, to reduce the risk that mislabeling or cross-contamination of samples will compromise the results. For example, any physician's office, laboratory, or hospital could tag samples immediately after collection, and the tags could be confirmed at the time of analysis. Similarly, samples containing nucleic acids collected at a crime scene could be tagged as soon as practicable, to ensure that the samples could not be mislabeled or tampered with. Detection of the tag upon each transfer of the sample from one party to another could be used to establish chain of custody of the sample.

Kits

Kits according to the invention can include one or more reagents useful for practicing one or more of the methods described herein. A kit generally includes a package with one or more containers holding the reagent(s) (e.g., primers), as one or more separate compositions or, optionally, as admixture where the compatibility of the reagents will allow. The kit can also include other material(s) that may be desirable from a user standpoint, such as a buffer(s), a diluent(s), a standard(s), and/or any other material useful in sample processing, washing, or conducting any other step of the method. In specific embodiments, the kit includes one or more matrix-type microfluidic devices discussed above.

In particular embodiments, a kit includes a forward primer and a reverse primer, wherein each primer includes a target-specific portion and a common sequence 5' of the target-specific portion. In certain embodiments, the common sequence includes a transposon sequence, such as, e.g., AGATGTGTNNNAGAGACAG-3' (SEQ ID NO:1) or, more specifically, 5'-AGATGTGTATAAGAGACAG-3' (SEQ ID NO:2).

In some embodiments, the forward primer and/or the reverse primer for each target nucleic acid include(s) a tag nucleotide sequence 5' of the common sequence. If both primers include tag sequences, the tag sequences can be the same or different.

The forward and/or reverse primer can, in some embodiments, include an additional nucleotide sequence 3' of the tag nucleotide sequence. Where the target amplicons are to be sequenced, one or both primers can include additional nucleotide sequence(s) that are binding site(s) for DNA sequencing primers. For example a forward primer can include a first binding site for a first DNA sequencing primer, and/or the reverse primer can include a second binding site for a second DNA sequencing primer.

The forward or reverse primer can additionally include a flow cell attachment site 5' of the tag nucleotide sequence to facilitate sequencing on the Illumina platform. In certain embodiments, the forward primer includes a first flow cell attachment site, and a second flow cell attachment site can be added to the amplicon via another primer.

A third primer can be included in the kit for the purpose of adding an additional nucleotide sequence of any type. For example, in an embodiment useful for carrying out 1-step addition of sequences for DNA sequencing, a third primer can include a tag-specific portion and a second additional nucleotide sequence 5' of the tag-specific portion. In various embodiments, the second additional nucleotide sequence comprises a barcode nucleotide sequence and/or a second flow cell attachment site, which can be different from the first flow cell attachment site. In particular embodiments, the second additional nucleotide sequence comprises a barcode nucleotide sequence 5' of the tag-specific portion, and a second flow cell attachment site 5' of the barcode nucleotide sequence.

In an embodiment useful for carrying out 2-step addition of sequences for DNA sequencing, a third primer can include a tag-specific portion, a barcode nucleotide sequence 3' of the tag-specific portion, and a second flow cell attachment site 3' of the barcode nucleotide sequence. Use of this primer after amplification with appropriate forward and reverse primers (described above and illustrated in FIG. 3) produces target amplicons having the structure: 5'-first nucleotide tag-first primer binding site-target nucleotide sequence-second primer binding site-second nucleotide tag-barcode nucleotide sequence-second flow cell attachment site-3'. In this case, the kit can include a fourth primer to be used in conjunction with the third primer to generate this amplicon. The fourth primer is typically specific for a sequence at the 3'end of the amplicon, such as the second flow cell attachment site.

Kits generally include instructions for carrying out one or more of the methods described herein. Instructions included in kits can be affixed to packaging material or can be included as a package insert. While the instructions are typically written or printed materials they are not limited to such. Any medium capable of storing such instructions and communicating them to an end user is contemplated by this invention. Such media include, but are not limited to, electronic storage media (e.g., magnetic discs, tapes, cartridges, chips), optical media (e.g., CD ROM), RF tags, and the like. As used herein, the term "instructions" can include the address of an internet site that provides the instructions.

It is understood that the examples and embodiments described herein are for illustrative purposes only and that various modifications or changes in light thereof will be suggested to persons skilled in the art and are to be included within the spirit and purview of this application and scope of the appended claims.

In addition, all other publications, patents, and patent applications cited herein are hereby incorporated by reference in their entirety for all purposes.

EXAMPLES

Example 1—Looping PCR to Reduce Amplicon Cross-Hybridization

Figures 4A, 4B:
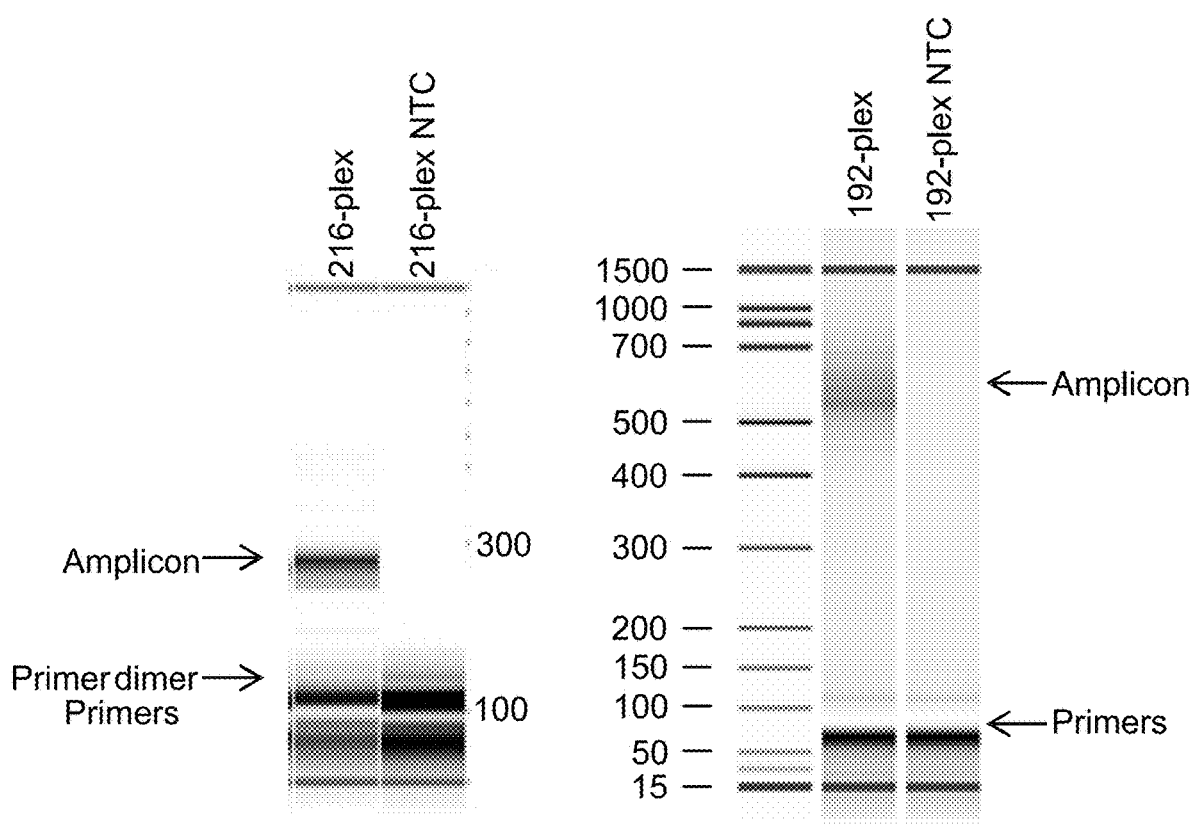
FIG. 4A-4B: PCR amplification specificity: non-looping vs. looping PCR. (A) 2-primer assay of 216-plex in a tube using primers with tags that cannot form a stem-loop yields an average amplicon size of 290 bp (about half the expected size). (B) 2-primer assay of 192-plex in a tube using primers with tags that form a stem-loop, as shown in FIG. 1, yields an average amplicon size of about 600 bp.

For compatibility with Illumina sequencing chemistry, the published tagged transposon sequence was used as a part of tagged specific primers in a common sequence in both forward and reverse primers (the transposon sequence is underlined):
Tag used for forward target-specific primer:
5'-TCGTCGGCAGCGTC<u>AGATGTGTATAAGAGACAG</u>-3' (SEQ ID NO:3)
Tag used for reverse target-specific primer:
5' GTCTCGTGGGCTCGG<u>AGATGTGTATAAGAGACAG</u>-3' (SEQ ID NO:4)
(The transposon sequence is that published for the NEXTERA" DNA Sample Prep Kit.)
A stem loop will form from an amplified amplicon to suppress amplicon cross hybridization (FIG. 1). The common sequence in the primers also reduces the probability of primer dimer formation (FIG. 4).

Figure 5:
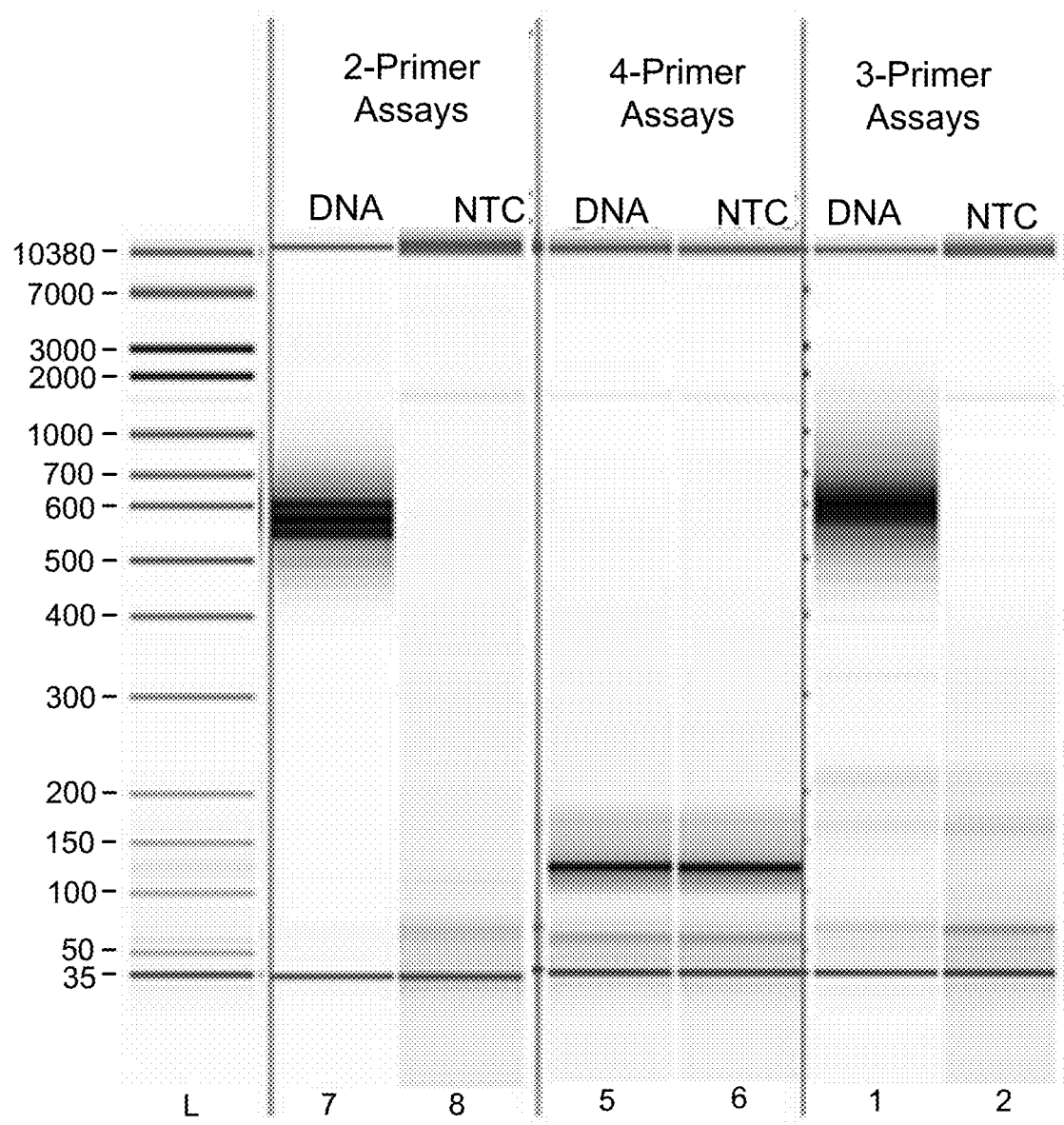
FIG. 5: Gel image of 192-plex assay in tube with 2-primer, 3-primer (FIG. 2), and 4-primer assay scheme.

Example 2—3-Primer Chemistry Facilitates On-Chip Barcoding with Minimal Primer-Dimer Formation The existing ACCESS ARRAY™ multiplex chemistry can provides 10-plex using 4 primers and two PCR steps. In the first step, PCR is conducted on the ACCESS ARRAY™ IFC, and in the second step, harvested samples are barcoded in a PCR plate. This workflow can be used for 10-20-plex, but with less-than-desired sequencing specificity, and is prone to sample cross-contamination. To achieve 1-step sample barcoding with reduced non-specific amplification, a 1-step, 3-primer scheme was proposed. FIG. 2 shows this 1-step, 3-primer PCR barcoding scheme. The 1-step, 3-primer approach was used in 192-plex and produced specific products that were comparable to a 2-primer reaction (without barcodes), as shown in FIG. 5. By contrast, a 1-step, 4-primer assay failed to generate a PCR product in a 192-plex reaction.

Figure 6:
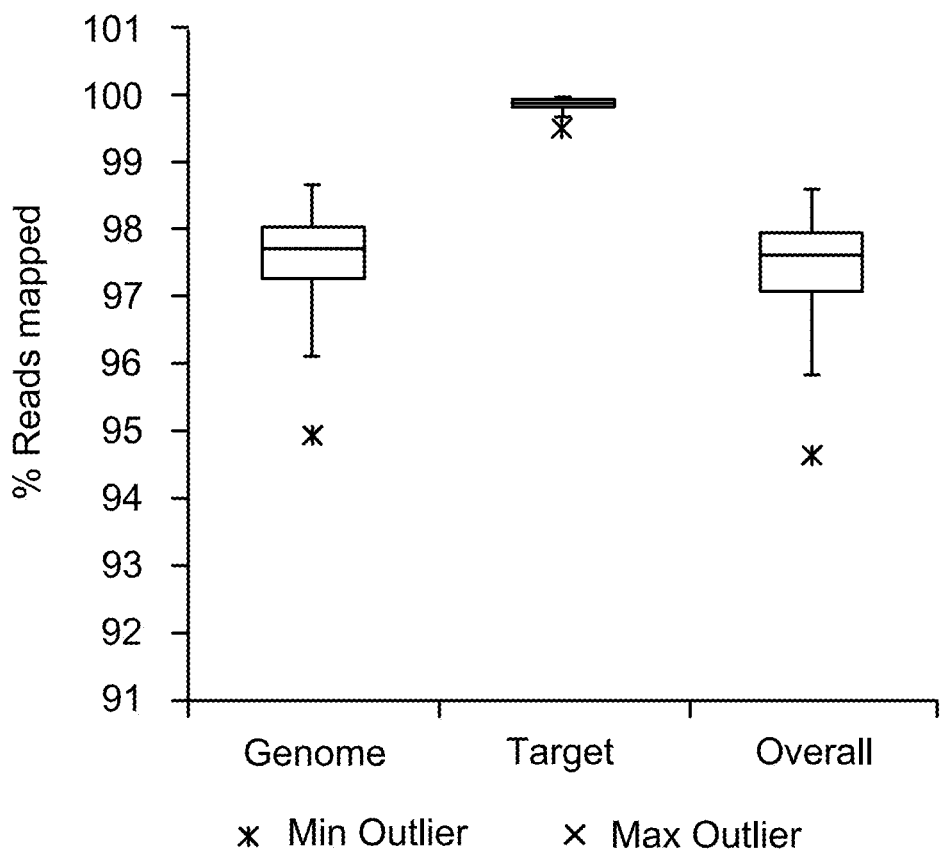
FIG. 6: Sequencing specificity of "super-plex" (highly multiplexed) reactions. Mapping rates of super-plex libraries generated on ACCESS ARRAY™ IFC (Integrated Fluidic Circuit) with the modified 3-primer on-chip barcoding scheme shown in FIG. 3. Multiplex level ranged from 78-plex to 168-plex with a total of 1075 reactions.

The sequencing data of the 1-step, 3-primer 192-plex reactions exhibited a >95% mapping rate to targets. However, the cost of the forward primers is very high due to their length. Therefore, a modified 2-step scheme was employed for the super-plex target sequencing library preparation, as shown in FIG. 3. The barcoded amplicon libraries were generated in a 3-primer reaction on an ACCESS ARRAY™ IFC, harvested in pools, and then the pooled libraries were further amplified in one tube to add sequencing adaptors. The products of the 2-step scheme exhibited a greater than 95% mapping rate to both genome and targets as shown in FIG. 6.

Figure 7:
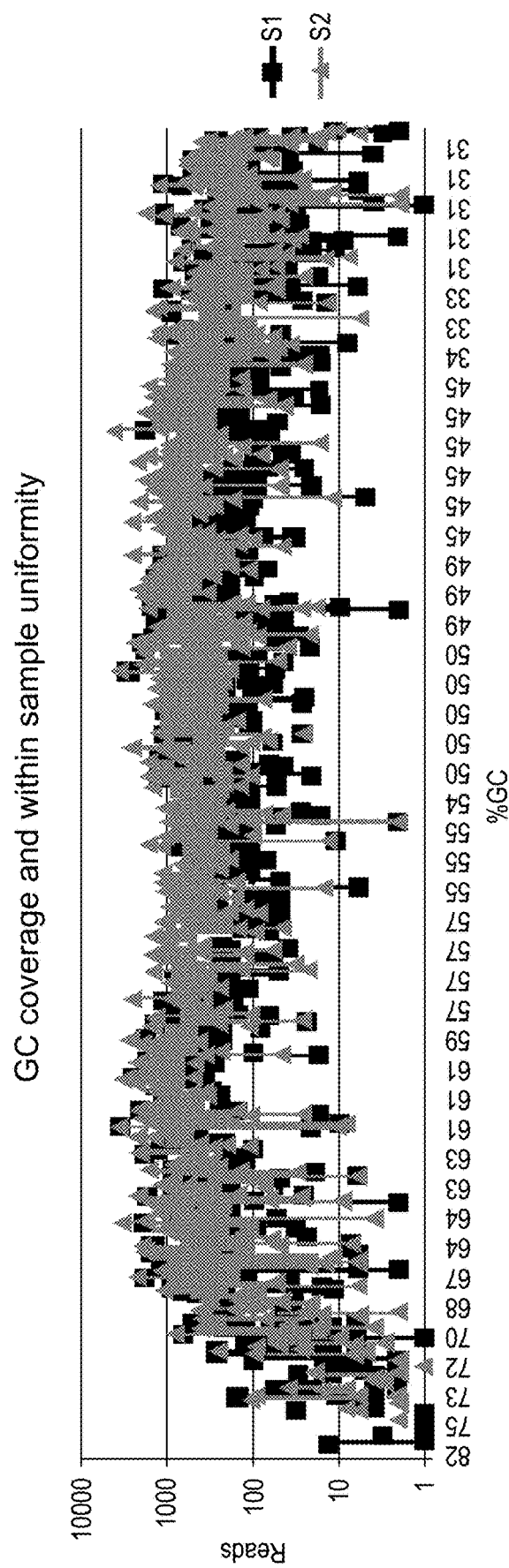
FIG. 7: GC coverage and amplification uniformity of super-plex PCR. Two samples are sorted by GC content of amplicons with average 500 bp. The GC contents of 1075 amplicons range to 25-82%.

Example 3—Addition of 2-Pyrrolidinone or a Mix of 2-Pyrrolidinone with Trehalose to the PCR Reaction to Amplify Amplicons with >65% GC Content Amplification of amplicons with high GC contents has been challenging in PCR field, particularly in multiplex assays. The challenge is to amplify amplicons with high GC contents without sacrificing those with low GC contents. To improve the GC coverage, 2-pyrrolidinone was added to a mixture of 1% 2-pyrrolidine and 150 mM trehalose to the commercial PCR master mix. The optimized concentration of 2-pyrrolidinone is 1-2%. The GC contents of amplicons with average 500 bp are expanded to >70%, with minimal impact on amplicons with <40% GC as shown in FIG. 7.

Example 4—Thousands-Plex PCR in a Single Reaction Mixture

Figure 9A:
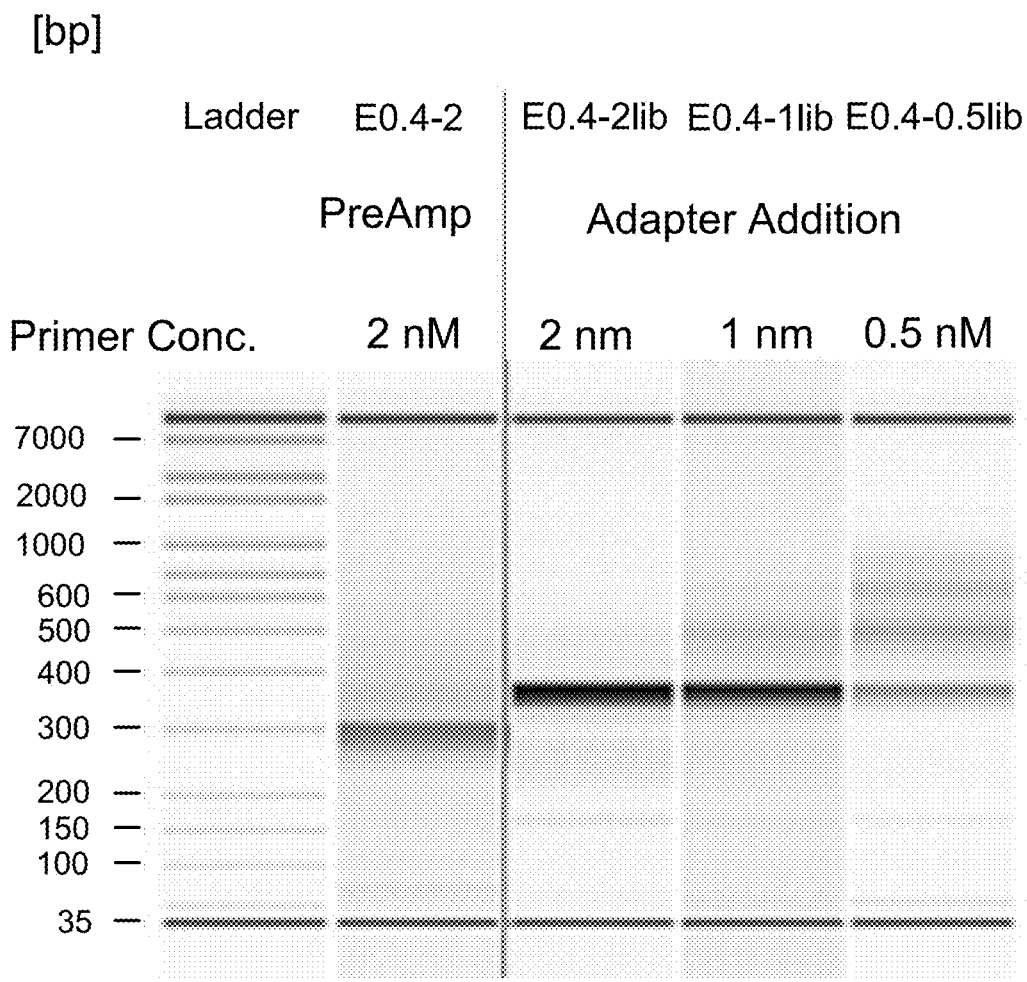
FIG. 9A-9D.
Figure 9B:
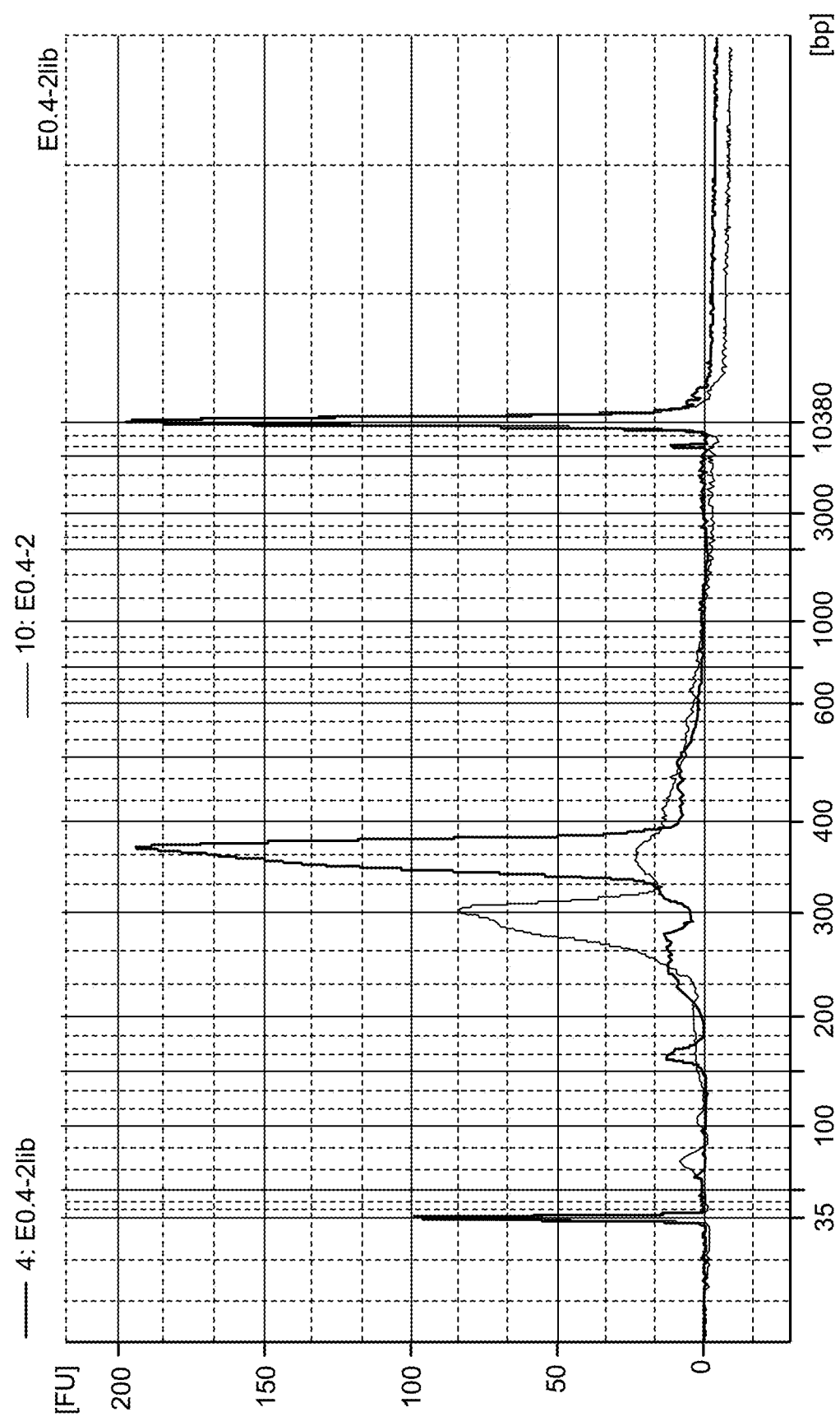
Figure 9C:
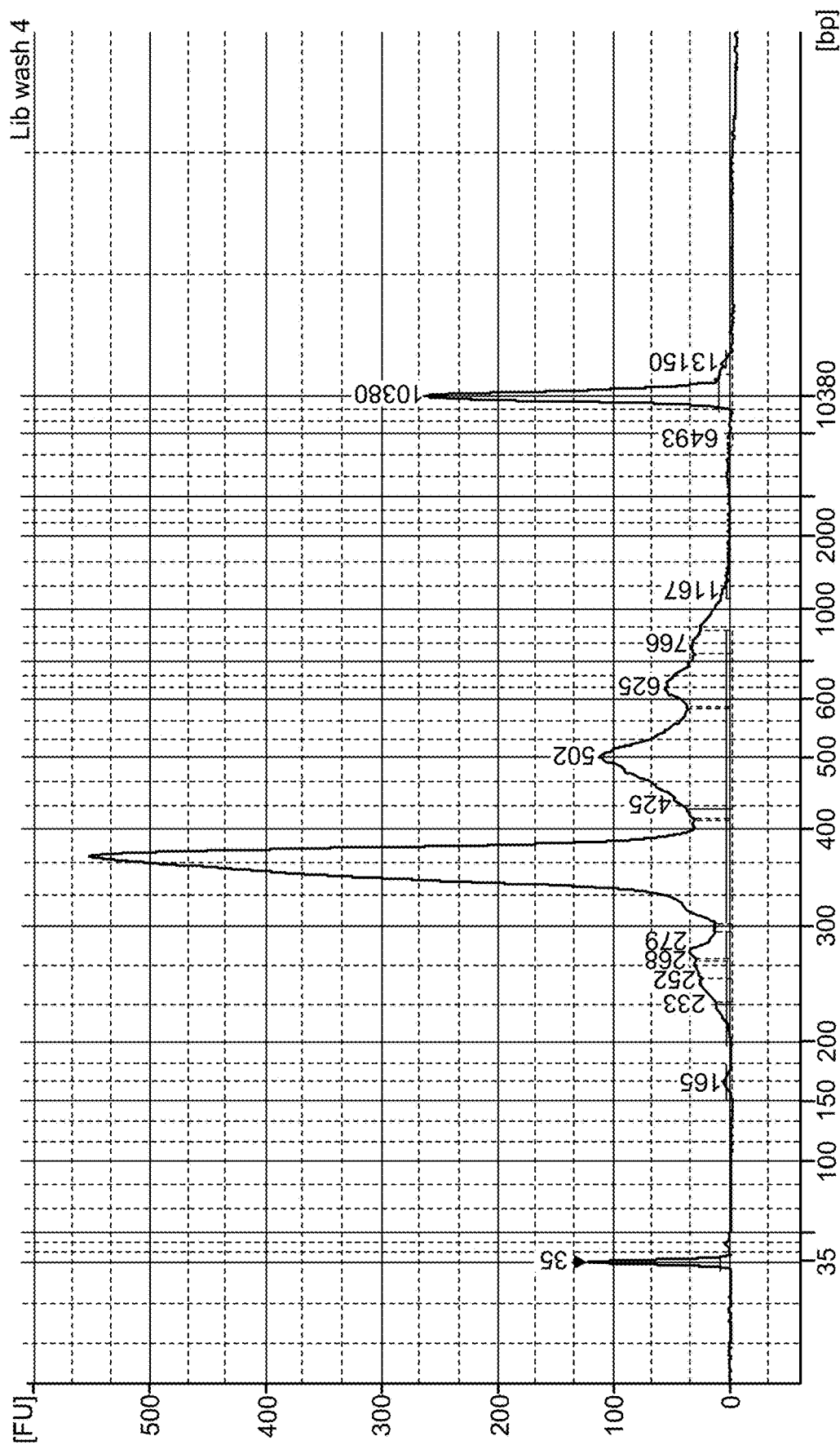
Figure 9D:
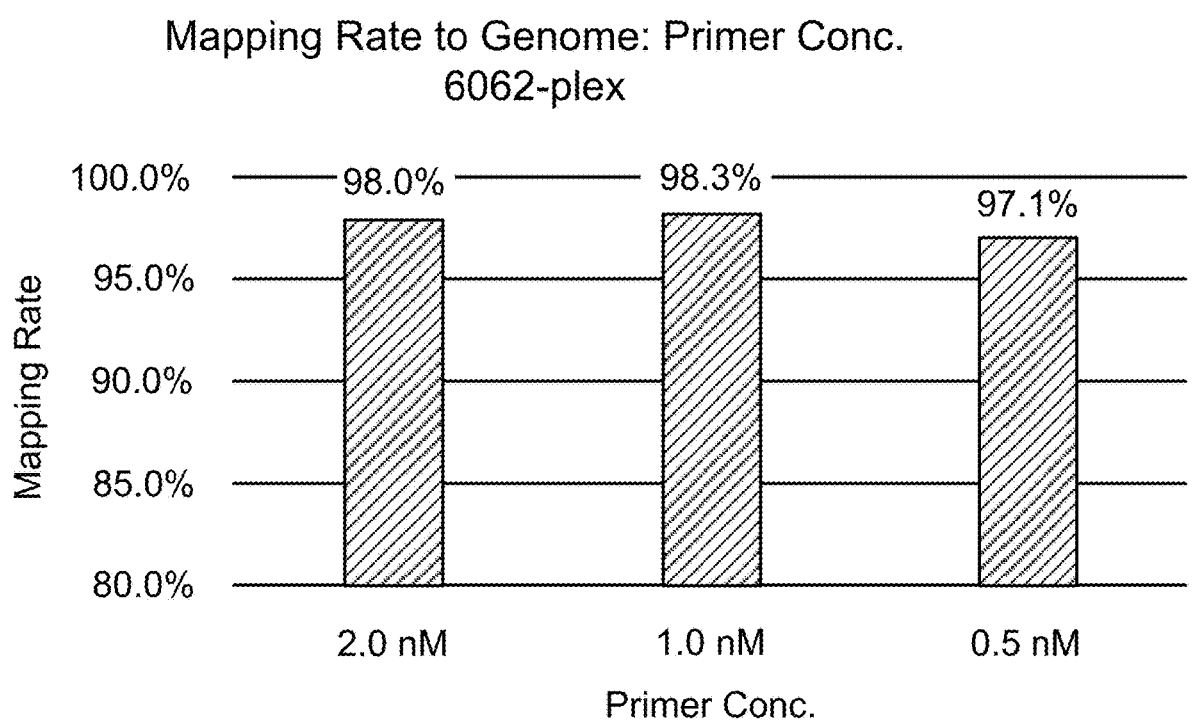

Looping PCR with 2-step addition of sequences for DNA sequencing was carried out essentially as described above and illustrated in FIG. 3. 6062 primer pairs were added to a single reaction tube. Multiple tubes were prepared with different PCR master mixes: (1) one with Aptataq DNA polymerase, (2) Thermo's PreAmp Master Mix, (3) 4×TSP Master Mix (used as 2×), and (4) Targeted DNA Seq Library reagent kit (PN101-2511). A 20-cycle PCR was used for the first step with the 6062 primer pairs, followed by 2× cleanups and adapter addition in a 10-cycle PCR for the second step. Similar results were observed with all 4 master mixes. A representative gel image and corresponding Bioanalyzer trace is shown in FIGS. 9A-9B. The results show that the 6062-plex amplification worked to produce a major band of amplicons in the expected 320-380 bp size range, when the primer concentration for the first step, 20-cycle PCR was 2 nM. Reducing this primer concentration to 1 nM or 0.5 nM produced greater amplicon overlapping, yielding an amplicon size range of 160-1000 bp, which was the expected size range for overlapped amplicons (see FIG. 9C). The sequencing mapping rate to the genome (determined using the Targeted DNA Seq Library reagent kit) is shown in FIG. 9D. This shows that very specific amplification at 6062-plex is achieved at primer concentrations of 0.5-2 nM.

common sequence, and a first or second nucleotide tag 5' of the DNA sequencing primer binding site, wherein the first and second nucleotide tags in the forward and reverse primers are different, wherein the common sequence is at least 8 nucleotides in length, and wherein the forward primer or the reverse primer additionally comprises a first flow cell attachment site 5' of the first nucleotide tag; and amplifying the target nucleic acid(s) to produce at least one target amplicon wherein a target nucleotide sequence is flanked by the common sequence on one end and its reverse complement on the other end, whereby a single strand of the target amplicon can form a stem loop structure, wherein the amplification is carried out using a third primer, wherein the third primer comprises a portion specific for the second nucleotide tag, a barcode nucleotide sequence 5' of the tag-specific portion, and a second flow cell attachment

What is claimed is:

1. A method for amplifying one or more target nucleic acids, the method comprising:

contacting sample nucleic acids with a forward primer and a reverse primer for each target nucleic acid, wherein each primer comprises a target-specific portion, a common sequence 5' of the target-specific portion, a DNA sequencing primer binding site 5' of the site 5' of the barcode nucleotide sequence, wherein the amplification produces target amplicons comprising the structure:

5'-first flow cell attachment site-first nucleotide tag-first DNA sequencing primer binding site-common sequence-target nucleotide sequence-reverse complement of common sequence-second DNA sequencing primer binding site-second nucleotide tag-barcode nucleotide sequence-second flow cell attachment site-3'.

2. The method of claim 1, wherein a plurality of target nucleic acids is amplified.

3. The method of claim 1, wherein a plurality of target nucleic acids is amplified in a single reaction mixture.

4. The method of claim 3, wherein at least 100 target nucleic acids are amplified in a single reaction mixture.

5. The method of claim 4, wherein at least 1000 target nucleic acids are amplified in a single reaction mixture.

6. The method of claim 1, wherein fewer than 17,000 target nucleic acids are amplified in a single reaction mixture.

7. The method of claim 1, wherein the common sequence comprises a transposon end sequence.

8. The method of claim 1, wherein amplification cross-hybridization is suppressed as compared to when amplification is carried out using primers containing only target-specific sequences.

9. The method of claim 1, wherein the average target amplicon size is greater than when amplification is carried out using primers containing only target-specific sequences.

10. The method of claim 1, wherein the amplification is carried out in a microfluidic device comprising a plurality of reaction chambers.

11. The method of claim 10, wherein amplification is carried out in multiplex within each of a plurality of reaction chambers.

12. The method of claim 11, wherein more than 100 target nucleic acids are amplified in each of the plurality of reaction chambers.

13. The method of claim 1, wherein the method is carried out to produce a DNA sequencing library.

14. The method of claim 1, wherein the method additionally comprises sequencing the target amplicons.

* * * * *

SEQUENCE LISTING

```
<160> NUMBER OF SEQ ID NOS: 4

<210> SEQ ID NO 1
<211> LENGTH: 19
<212> TYPE: DNA
<213> ORGANISM: Artificial Sequence
<220> FEATURE:
<223> OTHER INFORMATION: Transposon
<220> FEATURE:
<221> NAME/KEY: misc_feature
<222> LOCATION: (9)..(11)
<223> OTHER INFORMATION: n is a, c, g, or t

<400> SEQUENCE: 1
agatgtgtnn nagagacag                                                19

<210> SEQ ID NO 2
<211> LENGTH: 19
<212> TYPE: DNA
<213> ORGANISM: Artificial Sequence
<220> FEATURE:
<223> OTHER INFORMATION: Transposon

<400> SEQUENCE: 2
agatgtgtat aagagacag                                                19

<210> SEQ ID NO 3
<211> LENGTH: 33
<212> TYPE: DNA
<213> ORGANISM: Artificial Sequence
<220> FEATURE:
<223> OTHER INFORMATION: Tag for forward target-specific primer

<400> SEQUENCE: 3
tcgtcggcag cgtcagatgt gtataagaga cag                                33

<210> SEQ ID NO 4
<211> LENGTH: 34
<212> TYPE: DNA
<213> ORGANISM: Artificial Sequence
<220> FEATURE:
<223> OTHER INFORMATION: Tag for reverse target-specific primer

<400> SEQUENCE: 4
gtctcgtggg ctcggagatg tgtataagag acag                               34
```